US007993871B2

(12) United States Patent
Skiffington et al.

(10) Patent No.: US 7,993,871 B2
(45) Date of Patent: Aug. 9, 2011

(54) SAMPLING METHOD AND DEVICE

(75) Inventors: Richard T. Skiffington, North Reading, MA (US); Robert S. Salter, Reading, MA (US); John F. Fitchen, Medford, MA (US)

(73) Assignee: Charm Sciences, Inc., Lawrence, MA (US)

( * ) Notice: Subject to any disclaimer, the term of this patent is extended or adjusted under 35 U.S.C. 154(b) by 1056 days.

(21) Appl. No.: 11/793,638

(22) PCT Filed: Dec. 19, 2005

(86) PCT No.: PCT/US2005/046121
§ 371 (c)(1),
(2), (4) Date: Jun. 20, 2007

(87) PCT Pub. No.: WO2006/069053
PCT Pub. Date: Jun. 29, 2006

(65) Prior Publication Data
US 2008/0206740 A1    Aug. 28, 2008

Related U.S. Application Data

(60) Provisional application No. 60/638,430, filed on Dec. 22, 2004, provisional application No. 60/711,199, filed on Aug. 25, 2005.

(51) Int. Cl.
*C12Q 1/24* (2006.01)
*C12M 1/30* (2006.01)
*G01N 1/02* (2006.01)

(52) U.S. Cl. ............... 435/30; 435/287.4; 435/287.6; 435/309.1; 422/411; 600/572; 436/165

(58) Field of Classification Search ............... 435/287.4, 435/287.6, 309.1, 30; 600/572; 422/411; 436/165
See application file for complete search history.

(56) References Cited

U.S. PATENT DOCUMENTS

| | | |
|---|---|---|
| 3,163,160 A | 12/1964 | Cohen |
| 3,450,129 A | 6/1969 | Avery et al. |
| 3,666,631 A | 5/1972 | Rich et al. |
| 3,776,220 A | 12/1973 | Monaghan |
| 3,918,435 A | 11/1975 | Beall et al. |
| 3,954,564 A | 5/1976 | Mennen |
| 4,150,950 A | 4/1979 | Takeguchi et al. |
| 4,311,792 A | 1/1982 | Avery |
| 4,312,950 A | 1/1982 | Snyder et al. |
| 4,353,868 A | 10/1982 | Joslin et al. |
| 4,387,725 A | 6/1983 | Mull |
| 4,409,988 A | 10/1983 | Greenspan |
| 4,436,243 A | 3/1984 | Nason et al. |

(Continued)

FOREIGN PATENT DOCUMENTS
EP    0155747 A1    9/1985
(Continued)

OTHER PUBLICATIONS

International Search Report (Form: PCT/ISA/210) regarding application No. PCT/US05/46121 (Aug. 9, 2006).

(Continued)

*Primary Examiner* — William H Beisner
(74) *Attorney, Agent, or Firm* — Richard J. Long

(57) ABSTRACT

Disclosed herein is test device and method for detection of sample analytes in which after sampling has occurred a closure is provided. Such a test device and method can be usefully employed to detect a variety of analytes including microorganisms.

22 Claims, 23 Drawing Sheets

U.S. PATENT DOCUMENTS

| | | |
|---|---|---|
| 4,610,171 A | 9/1986 | Nason |
| 4,707,450 A | 11/1987 | Nason |
| 4,749,655 A | 6/1988 | Monthony et al. |
| 4,770,853 A | 9/1988 | Bernstein |
| 4,790,640 A | 12/1988 | Nason |
| 4,803,048 A | 2/1989 | Nason |
| 4,978,504 A | 12/1990 | Nason |
| 5,078,968 A | 1/1992 | Nason |
| 5,091,316 A | 2/1992 | Monthony et al. |
| 5,096,062 A | 3/1992 | Burkardt et al. |
| 5,169,789 A | 12/1992 | Bernstein |
| 5,223,401 A | 6/1993 | Foltz et al. |
| 5,223,402 A | 6/1993 | Abbas et al. |
| 5,238,649 A | 8/1993 | Nason |
| 5,266,266 A | 11/1993 | Nason |
| 5,616,499 A | 4/1997 | Eckner et al. |
| 5,827,675 A | 10/1998 | Skiffington et al. |
| 5,869,003 A | 2/1999 | Nason |
| 5,879,635 A | 3/1999 | Nason |
| 5,965,453 A | 10/1999 | Skiffington et al. |
| 6,197,574 B1 | 3/2001 | Miyamoto et al. |
| 6,248,294 B1 | 6/2001 | Nason |
| 6,372,511 B1 | 4/2002 | Silver et al. |
| 2003/0143752 A1 | 7/2003 | Feldsine et al. |

FOREIGN PATENT DOCUMENTS

| | | |
|---|---|---|
| EP | 0321145 A2 | 6/1989 |
| EP | 0592503 B1 | 4/1996 |
| EP | 0717840 B1 | 11/1998 |
| JP | 407059555 A | 3/1995 |
| WO | WO-93/00994 | 1/1993 |
| WO | WO-93/09431 | 5/1993 |
| WO | WO-96/14570 | 5/1996 |
| WO | WO-97/23596 | 7/1997 |
| WO | WO-98/32020 | 7/1998 |
| WO | WO-2004/086979 A1 | 10/2004 |

OTHER PUBLICATIONS

Written Opinion of the ISA (Form: PCT/ISA/237) regarding application No. PCT/ISA/46121 (Aug. 9, 2006).

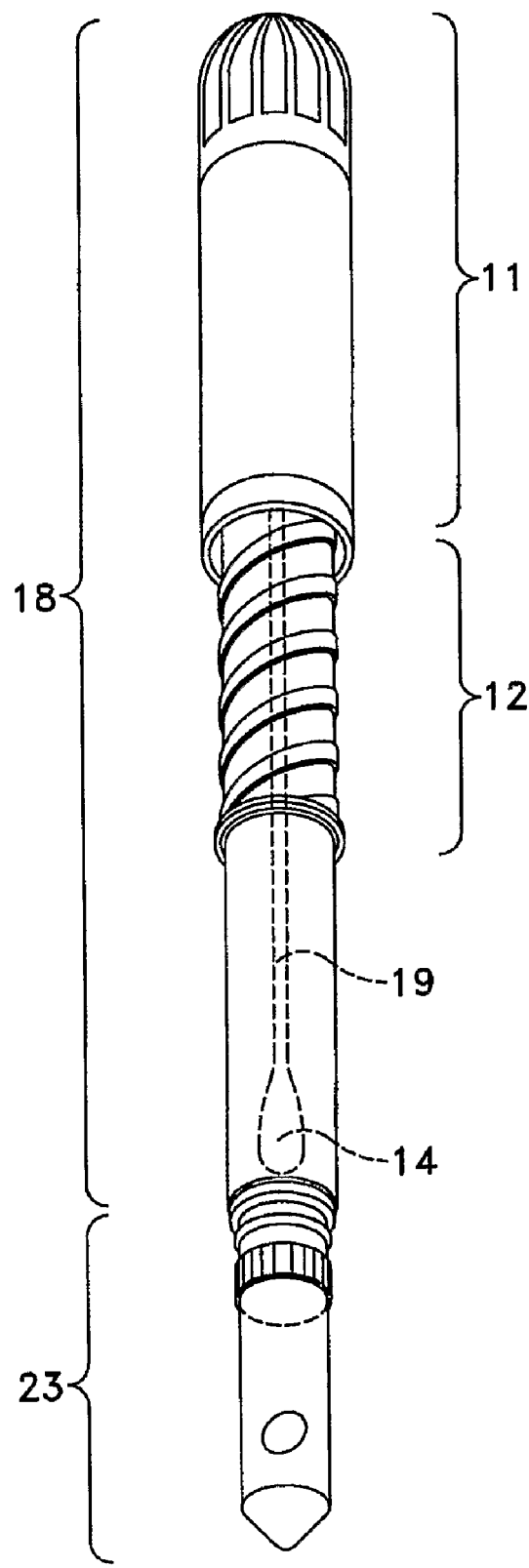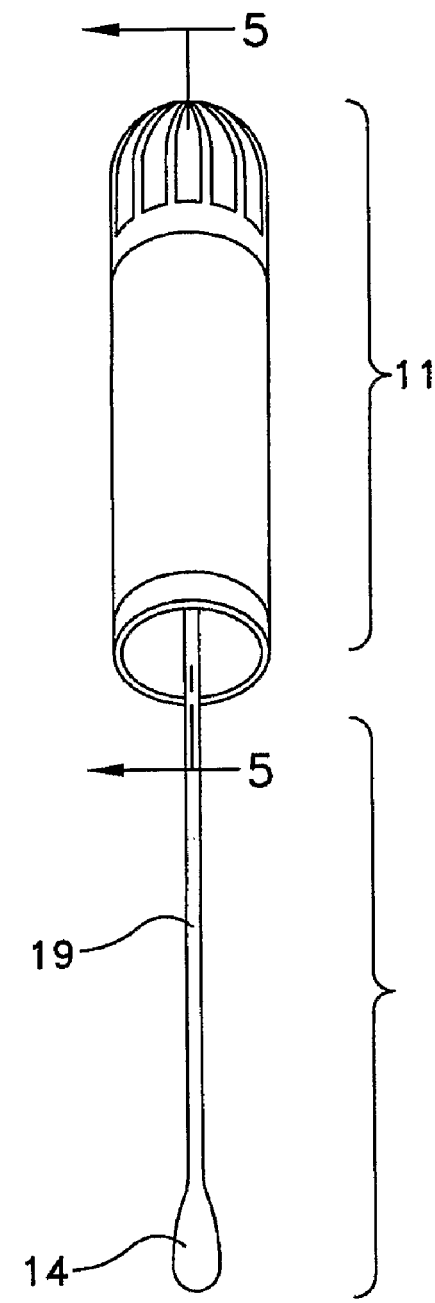
FIG. 3
FIG. 4

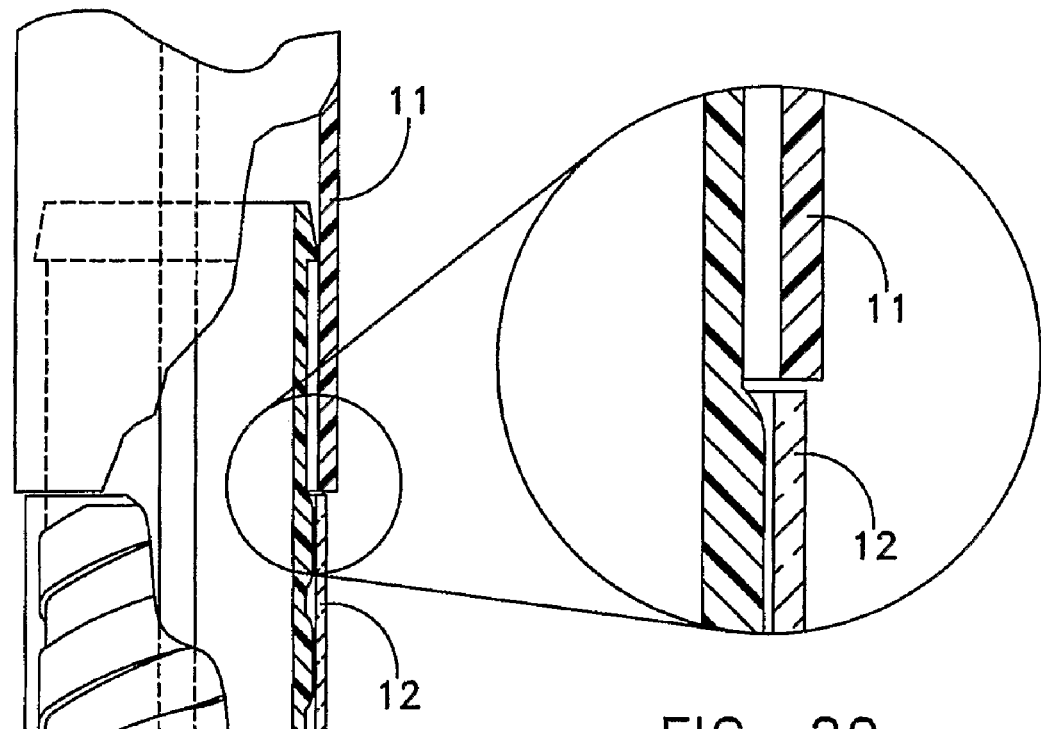
FIG. 20
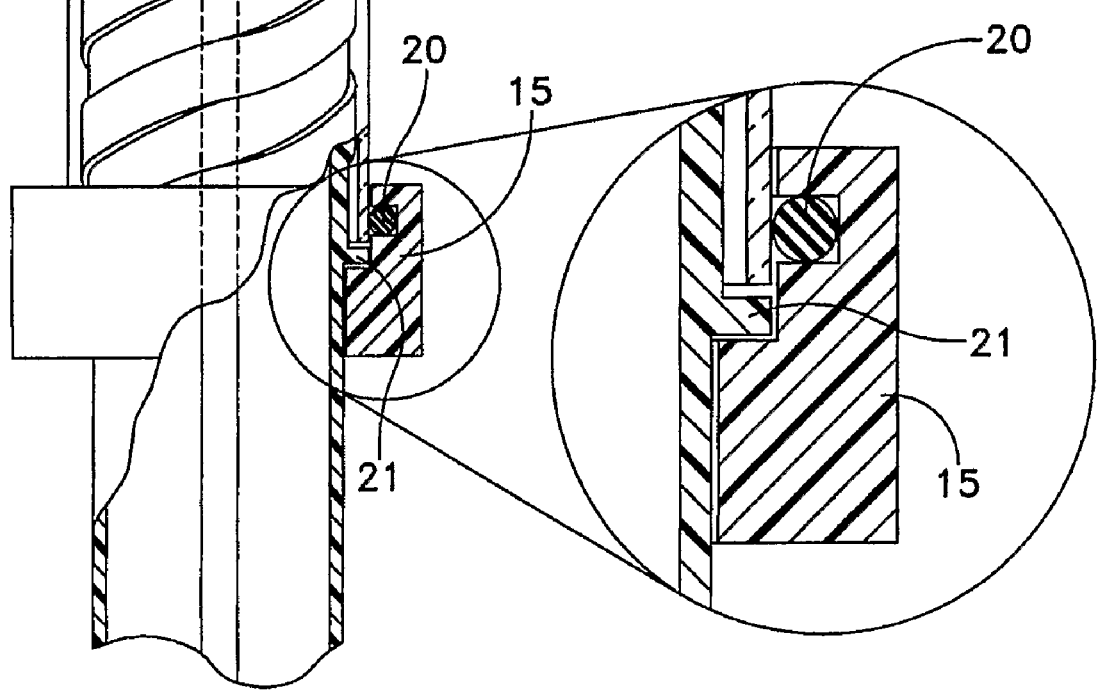
FIG. 19
FIG. 21

SAMPLING METHOD AND DEVICE

REFERENCE TO PRIOR APPLICATIONS

This application is based on and claims priority from U.S. Provisional Patent Application No. 60/638,430, filed Dec. 22, 2004, and U.S. Provisional Patent Application No. 60/711,199, filed Aug. 25, 2005, the teachings of both of which are incorporated herein by this reference.

TECHNICAL FIELD

This application relates to methods and devices for sampling surfaces and materials to detect analytes on the sampled surface or within the sampled materials.

BACKGROUND

Devices and methods for sampling surfaces and materials include self-contained, single service swabs for removing a sample from a surface and detecting adenosine triphosphate (ATP) in the sample by measuring the reaction of sample ATP with luciferin-luciferase to generate luminescence (light). The light from the reaction can be detected using an analyzer such as a luminometer, photodiode or photomultiplier. It is desirable to provide similar such devices and methods that are adapted to provide a stable test unit, for example one that will not leak and/or engage prematurely. Such a test unit can allow for culturing and/or detecting possibly hazardous microbes; maintaining the integrity of samples in non-laboratory conditions; transporting test samples such as DNA samples for later testing, for example in forensics; and maintaining samples in extreme conditions such as occur during space travel. It is also beneficial to provide a means to eliminate or reduce the risk that hazardous substances, for example cultured pathogens, will be released into the environment from the test unit.

BRIEF DESCRIPTION OF THE FIGURES

FIG. 3 is a perspective view including a partial elevation view of a test unit with a probe in the pre-use position within the test unit.

FIG. 4 is a perspective view of the swab cover with attached probe disengaged from the test unit body.

FIG. 19 is an enlarged partial cross-sectional view of a test unit in the pre-use position.

FIG. 20 is an enlarged partial cross-sectional view of a section of FIG. 19.

FIG. 21 is an enlarged partial cross-sectional view of a section of FIG. 19.

SUMMARY

Figure 1:
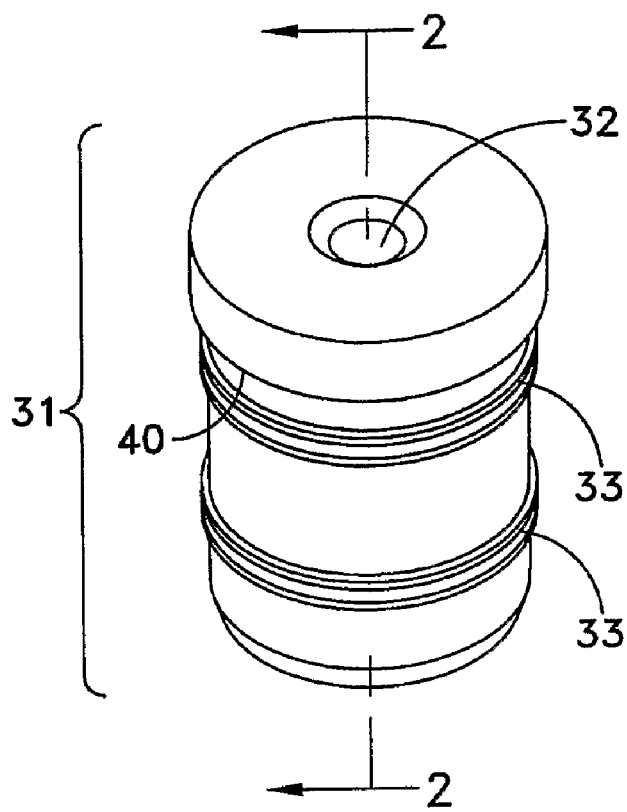
FIG. 1 is a perspective view of a plug that can be used to decrease or eliminate the risk of liquid leaking.

Aspects include detecting an analyte in a sample using an elongated test unit, the test unit including a hollow section with a first open end and second open end. A probe can be within the hollow section, the probe including a first probe end and a second probe end. A test unit cover can be attached to the first end of the probe and the cover can be designed to enclose the first open end of the hollow section. A test vial can be attached to the second open end of the hollow section and can contain reagents sealed therein by a frangible seal. A closure can be provided to prevent material such as liquid from entering and/or leaving the test unit. The probe can be used to obtain a test sample to provide admixture of the sample on the probe with reagents within the test vial. The probe can be so used by removing the probe from the test unit, collecting a sample onto the probe to provide a sample-probe, inserting the sample-probe into the test unit and moving the sample-probe longitudinally through the frangible test vial seal to contact the reagents. The longitudinal movement of the sample-probe can engage one or a variety of closures. The engagement of the closure can be simultaneous with contact of the sample-probe with the reagents. The closure can include a plug attached to the probe the plug designed and positioned so that moving the sample-probe longitudinally positions the plug to provide the closure, for example, between the peripheral wall of the plug and the inner diameter wall of the hollow section of the test unit. A closure can also be provided using an o-ring within an o-ring holder, the o-ring holder surrounding the test unit so that the test unit cover is secured into the o-ring holder to form the closure.

DESCRIPTION

Disclosed herein is a test unit, a test system and a test method for sampling a material or a surface of a material and detecting one or more analytes within the sample. Possible analytes include, but are not limited to, adenosine triphosphate, nucleic acids, small molecules such as antibiotics or toxins, proteins and/or microorganism. Various embodiments include allowing a sample to be taken from a material or surface and then contacted with reagents within a test unit while reducing or eliminating the risk of the reagents or the sample leaking out of the test unit by creating a closure. By closure we mean a barrier to substantially or completely prevent material, including liquid, from leaking out of the test unit and/or leaking into the test unit. Such embodiments can be useful when the reagents or analytes are dangerous or otherwise must be shielded from contact with the environment external to the test unit. Similarly, such embodiments can be used to protect the integrity of a collected sample, for example by protecting the sample from the environment external to the test unit.

U.S. Pat. Nos. 5,827,675, issued Oct. 27, 1998; 5,965,453, issued Oct. 12, 1999; 5,917,592, issued Jun. 29, 1999; and 6,055,050, issued Apr. 25, 2000, 6,180,395, issued Jan. 30, 2001, all hereby incorporated by reference, describe obtaining and testing samples, for example for the presence of adenosine triphosphate (ATP) and alkaline phosphatase (AP). One commercially available ATP sampling and detection method is known as the POCKETSWAB (POCKETSWAB is a registered trademark of Charm Sciences, Inc., Lawrence, Mass.). In one aspect, the POCKETSWAB is adapted, as further described herein, to obtain a sample for analysis to determine the presence of, for example, particular proteins, molecules, microbes, sugars and/or nucleic acids.

An embodiment includes collecting a sample, such as a biological specimen, using a probe. The probe can be provided within a test unit. After collecting the sample the probe containing the sample (the sample-probe) can be contacted with reagents, for example reagents provided within a test vial attached to the test unit. In an embodiment, a test vial is threadably attached to the bottom of the test unit. To avoid accidental removal of the test vial, whether or not threadably attached, the test vial can be secured to the bottom of the test unit, for example with adhesive such as an epoxy resin. A variety of techniques can be used, alone or with adhesive, to secure the test vial to the bottom portion of the test unit including encasing in shrink wrap. For example, a heat shrink can be used with tamper evident plastic such as cellulose or polyvinylchloride (PVC). The test vial can be a simple, single vial sealed at the top with a frangible seal and containing reagents therein. The test vial can also include one or more additional frangibly sealed reagent containers, hereinafter referred to as a niblet and/or additional internal frangible seals. Such niblets can be located above the test vial frangible seal, within the body of the test unit, or within the test vial.

Within the test vial that is secured to the test unit, can be a variety of substances, including: substances known in the art for nucleic acid detection; substances known in the art such as luciferin, luciferase and/or buffers for detecting ATP; and substances for culturing and/or detection of microorganisms, such as, for example, media known in the art for culturing and detection of *Listeria monocytogenes*.

Possibly useful culturing and/or detecting materials include those known in the art including those described in U.S. Pat. No. 5,728,542, issued Mar. 17, 1998, and U.S. Pat. No. 5,605,812, issued Feb. 25, 1997, the teachings of both of which are incorporated herein by this reference. When detecting microbes containment within a leak proof test unit is useful to protect against the escape of possibly harmful microbial culture into the external environment. The environmentally sealed test unit can also be useful in making the environment within the test unit favorable to microbial growth, for example anaerobic or facultative anaerobes, such as *Campylobacter*, can be grown. To provide a favorable environment for such microbes a valve can be built within the test unit, for example at the top of the test unit. The valve can be used to remove oxygen and/or add nitrogen to the internal environment of the test unit.

In another embodiment calorimetric or fluorometric indicators can be provided within the test unit such as in the test vial or in a niblet within or above the test vial. Such indicators can be general or specific to particular microbe genus or species, for example specific to particular proteins expressed by a microbe. Such indicators can also be used to indicate generally aerobic or anaerobic growth.

Generally, the test vial can include any of a variety of materials depending on the target of detection. The materials can be in a variety of forms including for example, solid, liquid, powder, emulsion, suspension, tablet or combinations thereof.

The test vial can include or be composed of a variety of materials such as organic polymeric materials including polypropylene, polyethylene, polybutyrate, polyvinylchloride and polyurethane. Materials and components can be irradiated or otherwise treated to reduce or eliminate possible contamination. Test vials and niblets can be a variety of sizes, volumes and colors. Unlike test vials used when luminescence or color is to be detected, test vials used for nucleic acid storage need not be transparent.

Various materials, such as liquids, can be sealed within the test vials, such as by using a frangible seal on top of the test vial. Material that can be used to frangibly seal the test vial include a variety or combination of organic polymeric materials such as silicone, rubber, polyurethane, polyvinylchloride or inorganic material such as wax or foil material. The frangible seal can be in a variety of forms including a membrane. The frangible seal can also be replaced by a disc or valve that can be held in place by a variety of techniques including chemical and mechanical techniques. The frangible seal can be adapted to be penetrated by the probe or by a separate instrument. In an example, the probe is moved longitudinally, for example threadably, to a selected position.

During the movement the frangible seal is punctured. After the frangible seal is punctured the sample is contacted with material within the test vial.

When the sample-probe contacts the material, for example reagents, within the test vial it may be desirable to: (i) engage or hold the sample-probe in place to maintain the sample-probe within the liquid in the test unit; and/or (ii) provide a closure to prevent liquid from leaking out of the test unit. In an embodiment, an o-ring style closure is provided. The closure can include an o-ring to lock the cover of the test unit in the engaged (post use) position with the probe within the test vial. The o-ring can be held within a device (an o-ring holder) that can be made of a variety or combination of materials including metal, rubber or plastic housing, for example polyvinylchloride. The o-ring holder can be a separate machined part or can be molded into the test unit. The o-ring holder can surround the test unit and can include an o-ring or other means for engaging the cover so as to form the closure. The o-ring holder can also include a shoulder/ridge to hold the o-ring holder in place, such as with a press-fit. The cover can be hollow and in the shape of a cylinder with an open end and a closed end. When in the engaged position the open end of the cover can move longitudinally to surround a portion of the test unit and engage within the o-ring holder forming a closure.

The o-ring can be made from a synthetic rubber material such as a fluoroelastomer, for example VITON (VITON is a registered trademark of E. I. Du Pont de Nemours & Company, Wilmington, Del.). Similarly, closures to engage the cover can be molded for a plastic-to-plastic interference fit connection. Such closures can be used alone or with additional closures to provide additional leak prevention such as in the form of an internal plug.

A plug type mechanism can be located within the cover and be designed to create a closure, such as an o-ring type closure, between the peripheral wall of the plug and the inner diameter wall of the body thereby reducing the risk of leakage into the external environment after the probe is engaged within the vial. Such a plug can be used alone or, for further leak prevention, in conjunction with an o-ring type closure mechanism surrounding the test unit as described above, to provide additional closure between the outer periphery of the test unit body and the inner wall of the swab cover.

The plug can be composed of a variety of materials including a variety of plastics, rubber and metal. The plug can be attached to the shaft of the probe, in a variety of ways and in a variety of configurations, so that the longitudinal movement of the probe to contact reagents also causes the plug to be positioned to form a closure. For example, the plug can be attached to the shaft of the probe such as through a bore in the plug center. The bore adapted for receiving the shaft, holding in place the shaft and forming a closure. The bore can be all the way through the plug so that the shaft can extend out of both ends of the plug, with one end of the shaft extending out to contact the cover and the other end extending out to the probe tip. In such an embodiment the peripheral wall of the probe can seal against the inner diameter wall of the plug bore, such as by using an o-ring type closure mechanism and/or glue, to prevent leakage. The plug can also include a ridge on one end of the plug so that a second closure is provided between the ridge of the plug and the top of one end of a hollow section of the test unit.

When using threads, or a sliding mechanism, or a weakened mechanical means to allow removal and reattachment of the cover portion of the test unit, it may be desired to provide a mechanism to prevent inadvertent engagement and puncturing of the frangible seal containing the reagents. In an embodiment a disposable impact sleeve (removable sleeve) can be made of, for example, a solid material such as an acrylic material or plastic material or plastic-like material. After removal of the cover portion the sleeve can be removed and discarded.

Examples of useful probes include a variety of swab like devices with an absorbent tip attached to a solid or semi-solid shaft. The probe can be composed of any or a combination of materials useful for absorbing, adsorbing or retaining a sample. Swab tip materials can include any type of porous material including rayon, Dacron, cotton, foam or a combination thereof. The tip can be pre-moistened with any one or more of a variety of liquids, depending on the need or application, or provided dry. If provided pre-moistened, the pre-moistening liquid can include, for example, buffer, sterile water, glycerin, diluents, wetting solutions, or other material desired to be mixed with the sample or useful for absorbing, neutralizing, stabilizing or maintaining a sample.

The probe can be hollow, for example the tip of the probe, such as a swab tip, can be located on the end of an elongated hollow straw-like shaft. When fluid flows from above the probe, the probe can be designed and positioned to allow fluid flow through the hollow shaft and into the swab tip. The shaft can also be designed to include within the hollow section a breakable cartridge containing reagents for mixing with a sample.

One or a plurality of additional frangibly sealed compartments (niblets) can also be provided within the test unit, for example within the top of the test vial or just above the test vial. The niblets can be composed of a variety of materials such as organic polymeric materials including polypropylene, polyethylene, polybutyrate, polyvinylchloride and polyurethane. Niblet and niblet materials can be irradiated or otherwise treated to reduce or eliminate possible contamination. Niblets can be a variety of sizes to hold a variety of quantities or volumes. Reagents within optional niblets can include a variety of materials depending on the target of detection. The materials within the niblets may be in the form of a solid, liquid, powder, emulsion, suspension, tablet or any combination thereof. Niblets can be sealed on both sides with frangible, puncturable seals. The frangible seals can be a variety or combination of organic polymeric materials such as silicone, rubber, polyurethane, polyvinylchloride or inorganic material such as wax or foil material. Use of optional niblets allows additional reagents or reagent combinations to be provided with the test unit separate from the reagents within the test vial. During test operation the reagents within the niblet are contacted by puncturing the frangible seal for example with a sample-probe.

In an embodiment a niblet is located immediately below the test vial frangible seal within the top portion of the test vial. When niblets are located below the test vial frangible seal, the collector will first puncture the test vial frangible seal and then puncture the top frangible seal on the optional first niblet. The sample-probe can be contacted with material within the niblet and at a selected time the sample-probe can be used to puncture the bottom end of the niblet releasing the contents toward the test vial. To provide additional frangibly sealed reagents a second or more niblets can be included. If only one niblet is present then the contents of the niblet, combined with the sample, can be mixed within the test vial and with other test reagents. Alternatively, no niblets are used and all reagents are frangibly sealed within the test vial.

The test unit into which the test vial can be attached and within which a probe can be contained can be composed of a variety or combination of organic polymeric materials such as polyurethane, polyvinylchloride, polypropylene, polyethylene, polybutyrate.

In an embodiment, a cover of a test unit, including the probe, can be disconnected from the bottom portion by employing threads, or a slidably fit mechanism, or a weakened mechanical section or other means, for example by removing or unsealing or ripping a tape holding the cover onto the bottom portion of the test unit. Having the bottom portion and cover portion threadably connected allows easy disconnecting and connecting. After removing the probe it can be used to obtain a sample and then reconnected to the bottom portion for example by utilizing threads.

A disinfectant can be provided in a variety of forms including tablet, liquid and powder. In tablet form the disinfectant can be provided inside the leak proof test unit, for example attached to the bottom of the plug or attached to the inner wall of the test unit. A tablet can be located so that when the test unit is oriented with the cap down and test vial up the material from the test vial can flow into contact with the tablet.

Translucent plastic can be used so that reactions within the test unit can be observed. For example, the disinfectant can include a dye that is visible to the user when contacted with material from within the test vial.

Other embodiments include using dissolvable tape, dissolvable plastic, such as cellulose based plastics, a burstable pouch or other similar containers that can contain a disinfectant that will be released either on contact with test material, such as liquid material, or that can be released upon application of pressure by a user. Similarly, if required, additional test reagents can be supplied within containers, such as burstable pouches, within a containment bag.

Other embodiments include a heater, such as a steam sterilizer, for example those available commercially and used to heat baby bottles, within which the test unit can be heated to eliminate or reduce the risk of contact with potentially dangerous microorganism.

Other embodiments include sealing the test unit within a leakproof zip-lock type bag and/or adhesive seal bag. Embodiments include using materials for containment bags from autoclavable plastic material such as polypropelyne. Such a bag can allow the customer to remove the test unit for use and then return the test unit to the bag such as for decontamination and disposal. Leak proof containment bag seals can be for example BITRAN (Associated Bag) leak proof zipper bag. Also within the containment bag can be a disinfectant such as a liquid in a burstable pouch that can allow the user to release the material from the test vial into contact with the disinfectant.

Containment bags and/or generally leak proof test unites are particularly useful when potentially dangerous organisms are targeted for detection. In an embodiment in which *Listeria monocytogenes* is targeted for detection the test vial can contain media for detection if *L. monocytogenes*. Such media can contain colorimetric reagents that provide a color change in the presence of a glucosidase.

In other embodiments, a variety of tests can be run using one sample for example tests for chemicals, biowarfare agents, explosives, metals, toxins, poisons. In another embodiment, the device and methods described herein can be used when sample preparation is common to a variety of tests.

DESCRIPTION OF THE DRAWINGS

FIG. 1 shows a plug 31 with bore 32 for probe shaft 19 and outer o-rings 33 to provide a closure against the inner diameter of the body of the test unit. Also shown is a plug cap 40 that both acts as a stopper to prevent the swab tip from contacting the bottom portion of the test vial and also can be an additional closure to prevent leakage.

Figure 2:
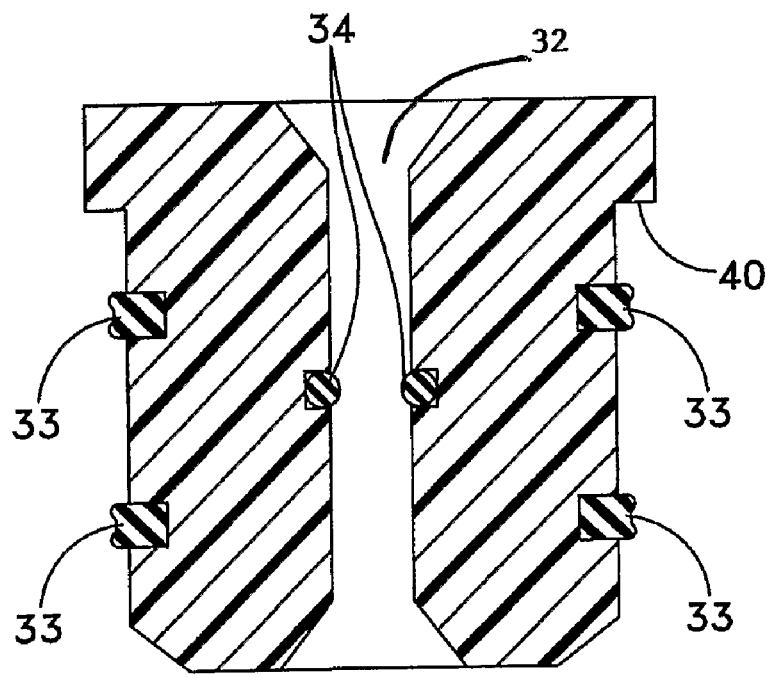
FIG. 2 is a cross-sectional view of the plug of FIG. 1.

FIG. 2 shows a plug 31 with outer o-rings 33 and inner o-rings 34 within the bore to provide a closure against the outer diameter of the probe shaft 19 and plug cap 40.

FIG. 3 shows a test unit in the pre-use position. The probe shaft 19 is attached to the cover 11 which, in the pre-use position is above threads 12. A test vial 23 is secured to the bottom of the unit 18.

FIG. 4 shows the cover 11 with probe (shaft 19 and tip 14) removed from the body of the test unit.

Figure 5:
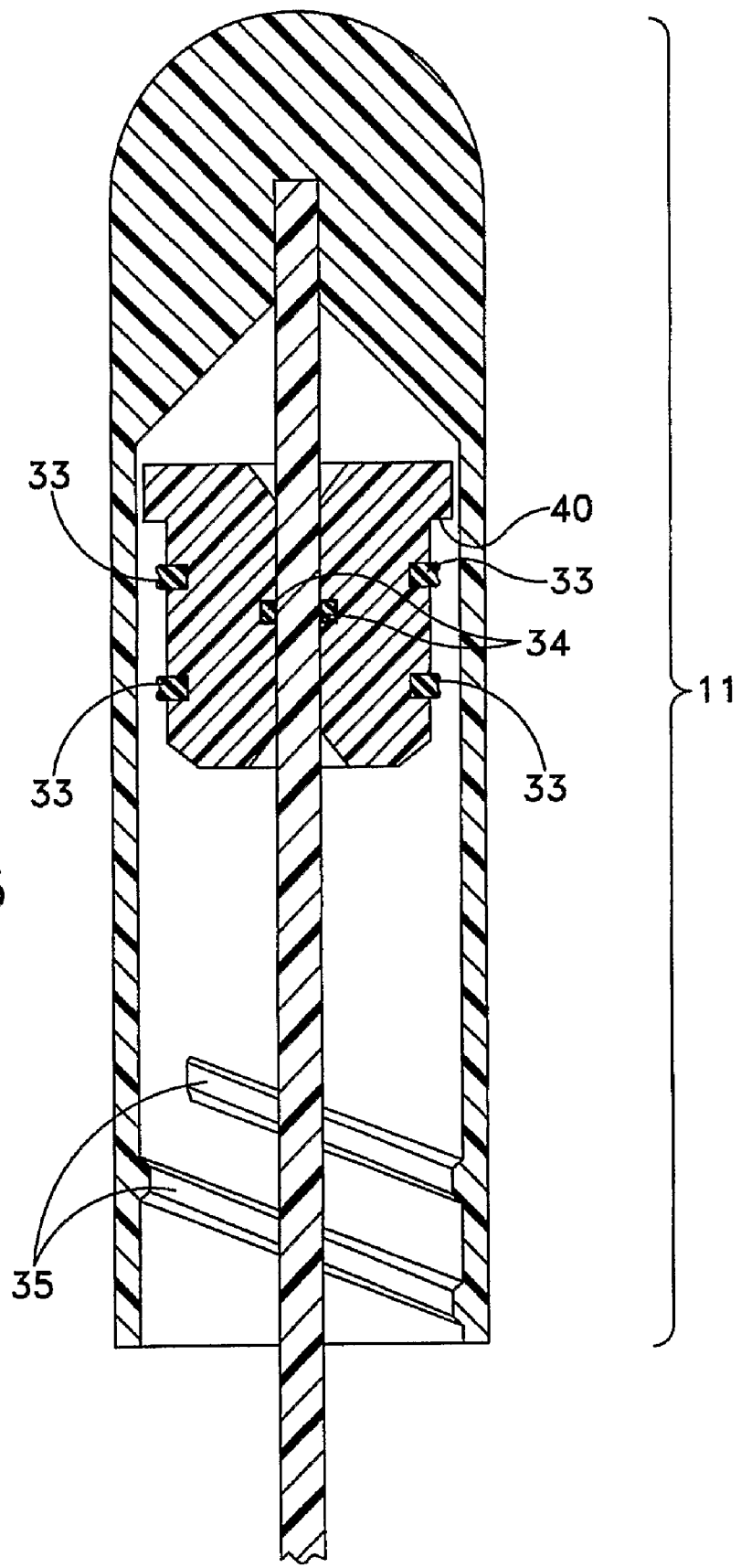
FIG. 5 is an enlarged cross-sectional view of the swab cover including plug in pre-use position.

FIG. 5 shows the pre-use position with the cover 11 with probe shaft 19 partially enclosed within plug 31 by inner o-rings 34. Also shown are outer o-rings 33 for providing a closure against the inner diameter of swab body and threads within cover 11 and plug cap 40. The shaft 19 is shown extending through the plug bore to contact the test unit cover 11 at one end of the shaft 19.

Figure 6:
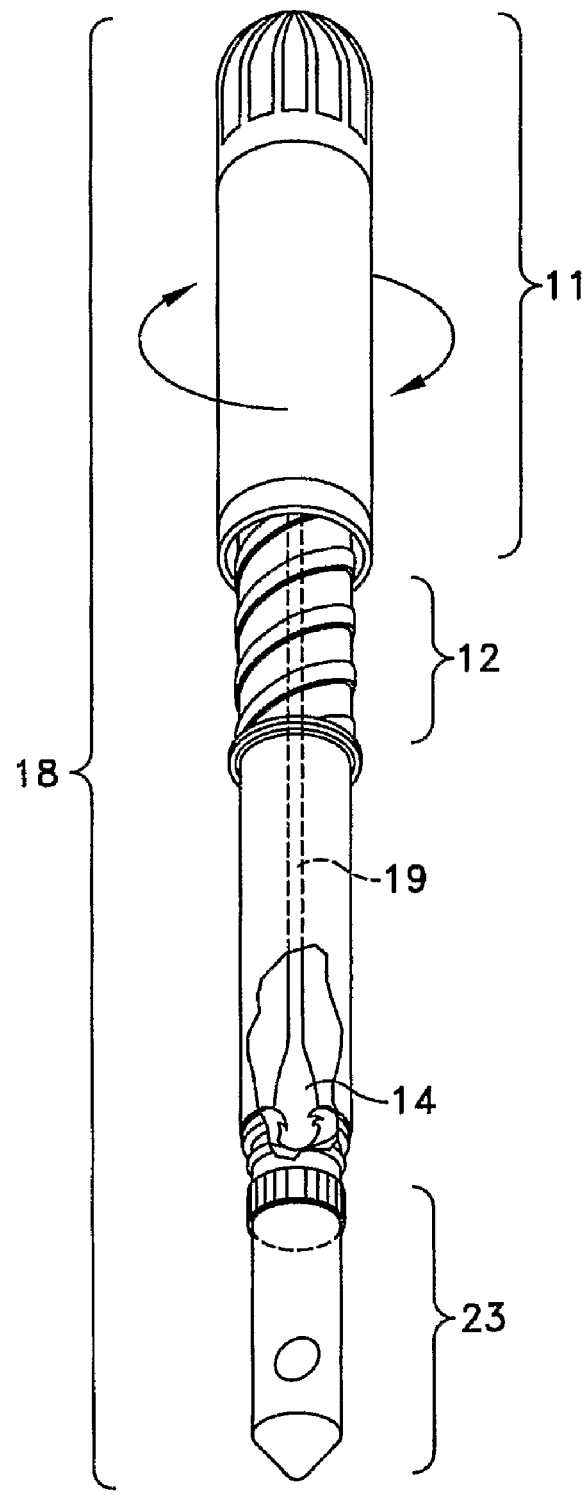
FIG. 6 is a perspective view including partial elevation view of a test unit with probe breaking through a frangible seal to contact reagent within the test unit.

FIG. 6 shows the cap 11 being turned to utilize the threads 12 on the test unit body and within the cover (FIG. 5) to drive the probe head 14 through frangible seals and into the test vial 23.

Figure 7:
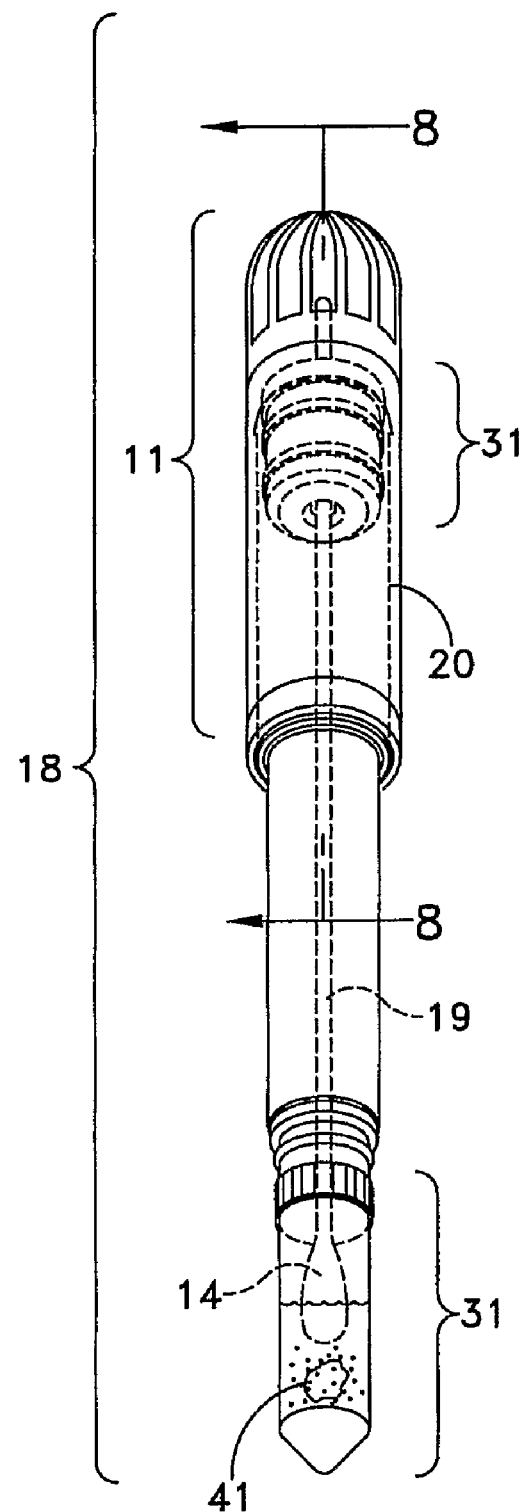
FIG. 7 is a perspective view including partial elevation view of a test unit in the use position with probe contacting reagents in the bottom of a test vial and showing the plug forming a closure.

FIG. 7 shows the plug in the engaged position within the cover 11 with probe head 14 contacting test reagents 41 within the test vial 23 thereby delivering a sample to the test reagents 41. Outer o-rings of the plug form a closure with the internal diameter 20 of the test unit body.

Figure 8:
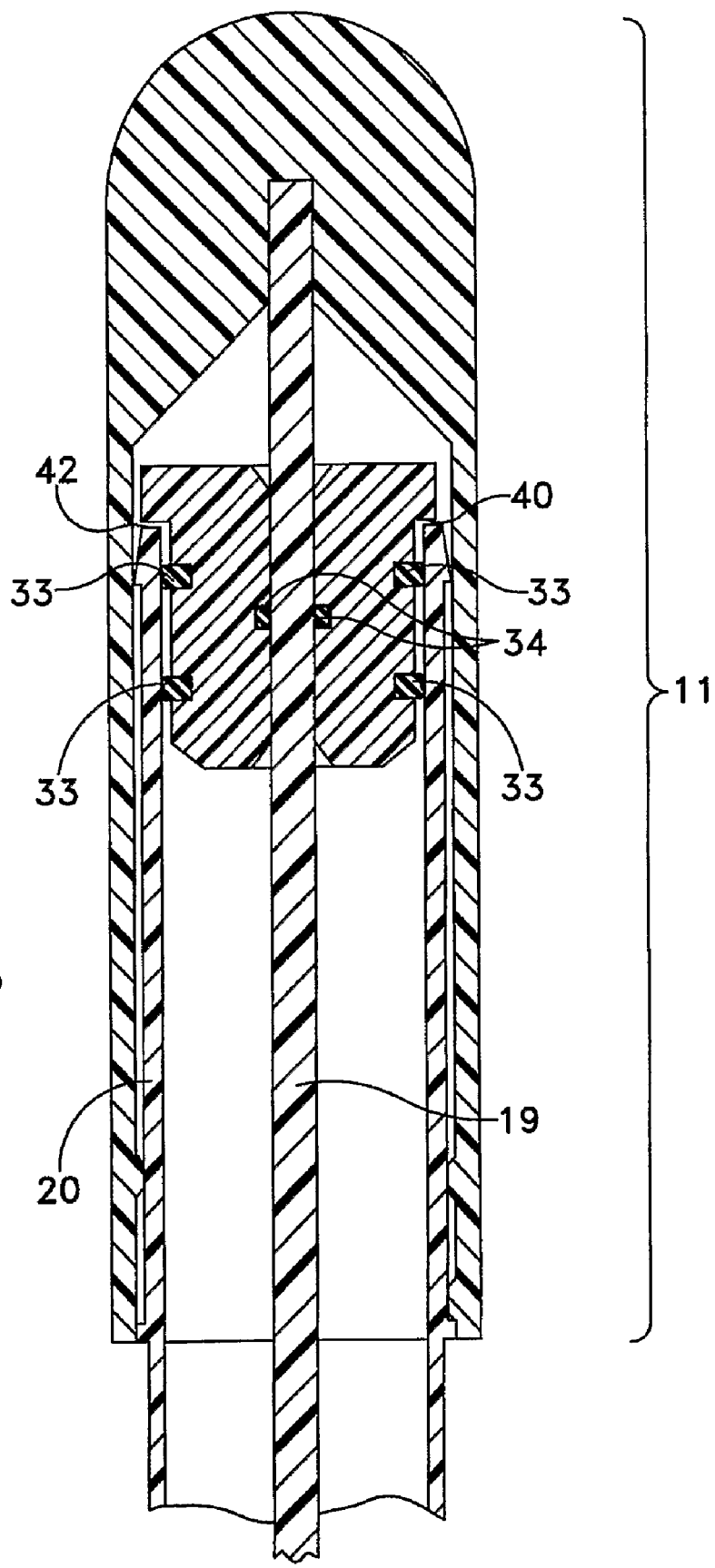
FIG. 8 is a cross-sectional view of the swab cover with plug forming a closure.
Figure 9:
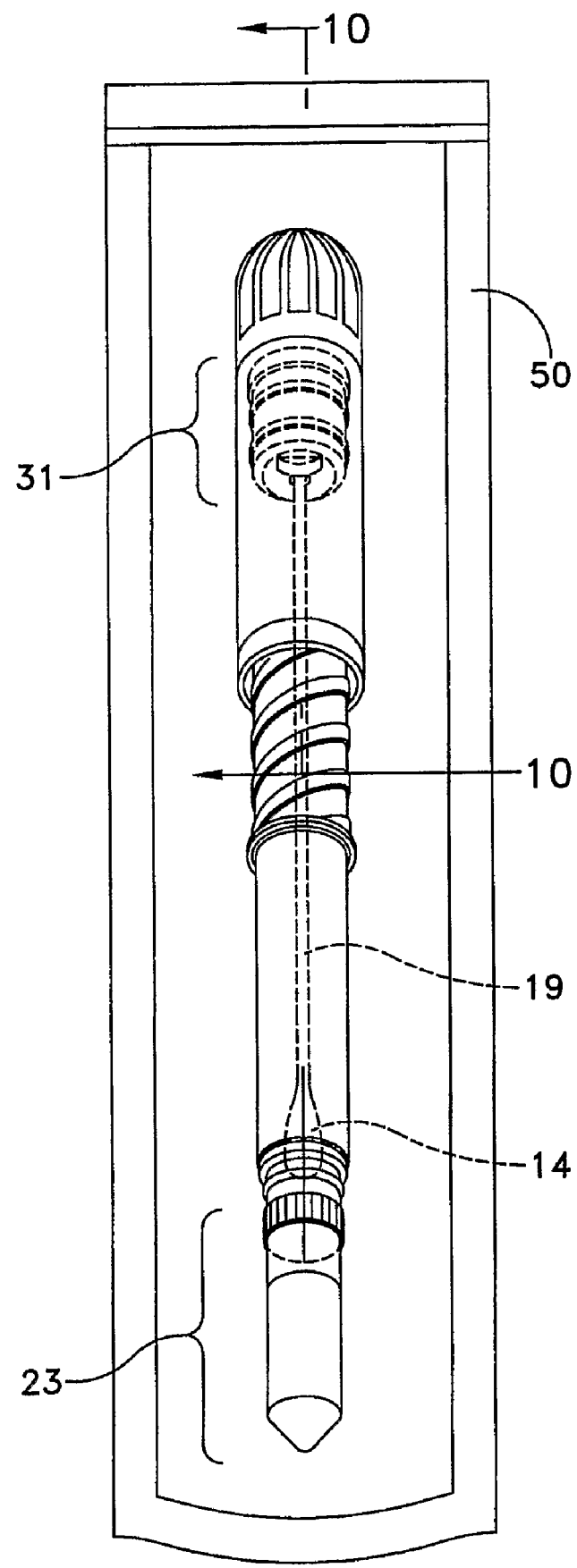
FIG. 9 is perspective view including partial elevation view of the test unit within a containment bag.

FIG. 8 shows a cross-section of the plug 31 in the engaged position within the cover 11 with probe shaft 19 partially enclosed via o-rings 34 within plug 31 and with plug 31 in the engaged position to provide a closure against the internal diameter 20 of the test unit body using the outer o-rings 33. Also shown is plug cap 40 positioned against one end 42 of a hollow section of the test unit. For clarity, FIG. 8 shows cap 40 not touching the one end 42 of the hollow section. In operation, cap 40 contacts 42. FIG. 9 shows the test unit within a sealed containment bag.

Figure 10:
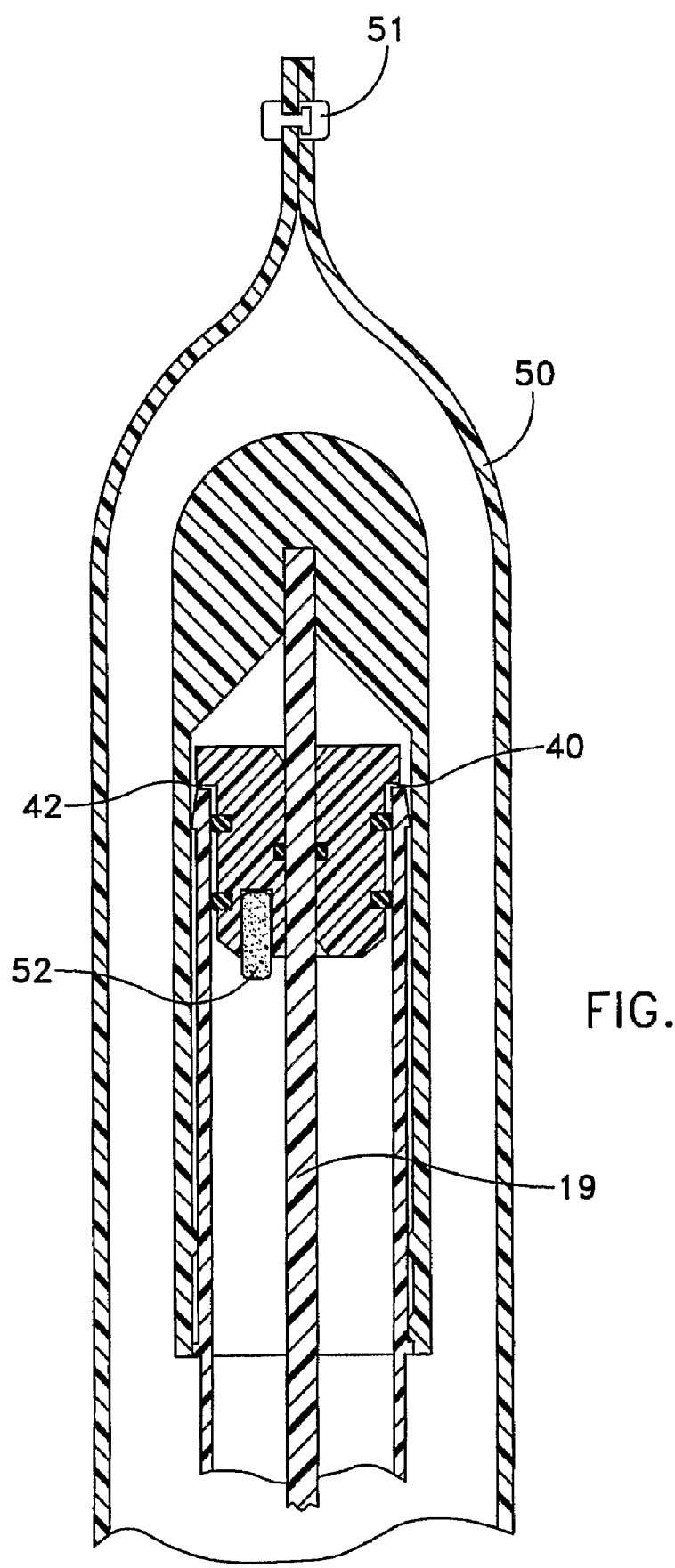
FIG. 10 is a cross-sectional view of the swab cover enclosed within a containment bag with plug forming a closure. A disinfectant tablet is shown attached to the bottom of the plug.

FIG. 10 shows the cover 11 of the test unit within the containment bag 50 including sealing means 51 at top allowing removal of test unit from containment bag for obtaining sample and placement into containment bag after sample is obtained. Also shown is disinfectant tablet 52 attached to the bottom of the plug 31.

Figure 11:
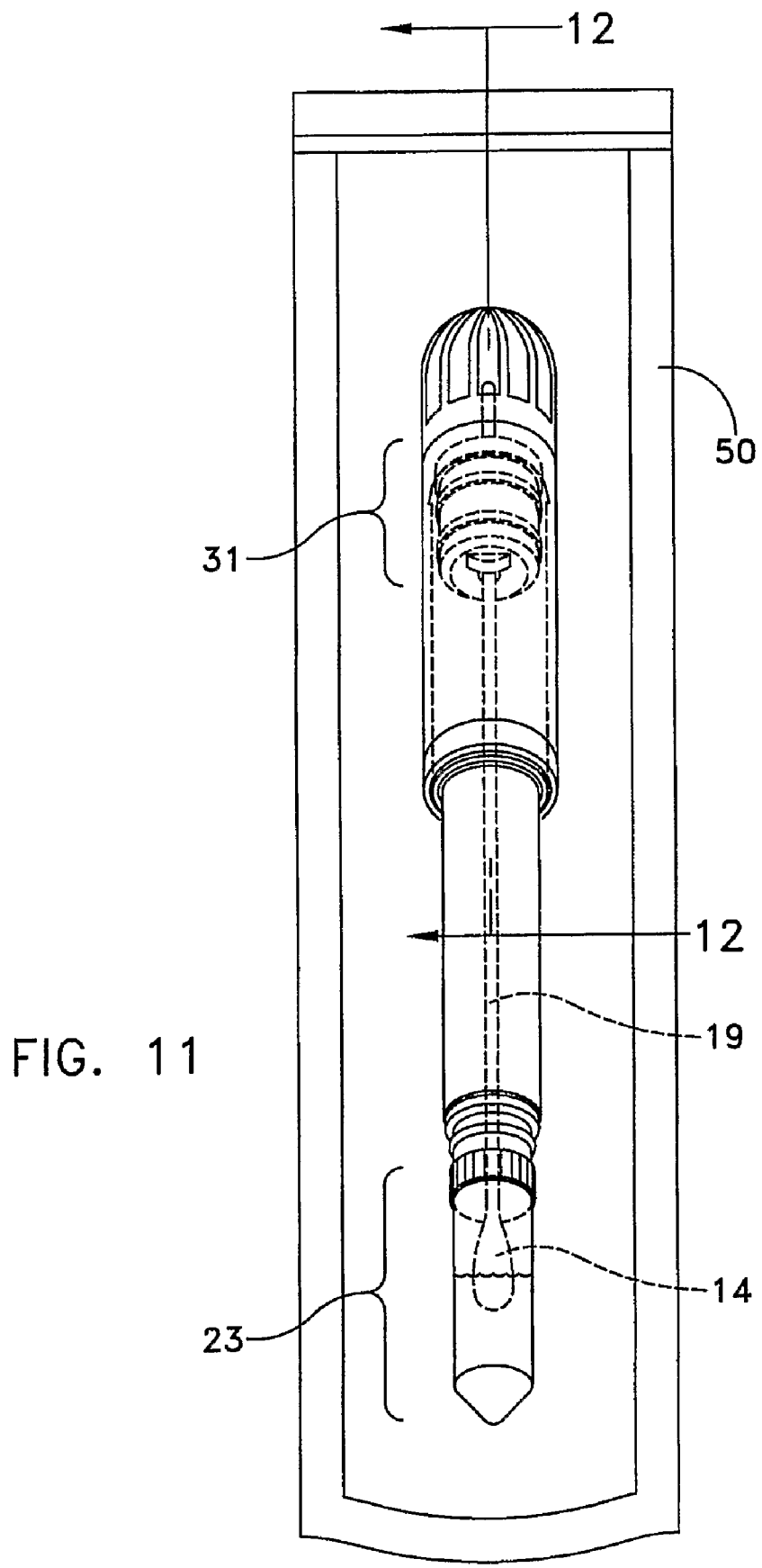
FIG. 11 is a perspective and partial elevation view of a test unit with probe engaged into the test vial and showing the plug forming a closure with the test unit sealed within a containment bag.

FIG. 11 shows the test unit within a sealed containment bag after removal to obtain sample, replacement into bag and contacting of sample with reagents within test vial with disinfectant table at bottom of plug.

Figure 12:
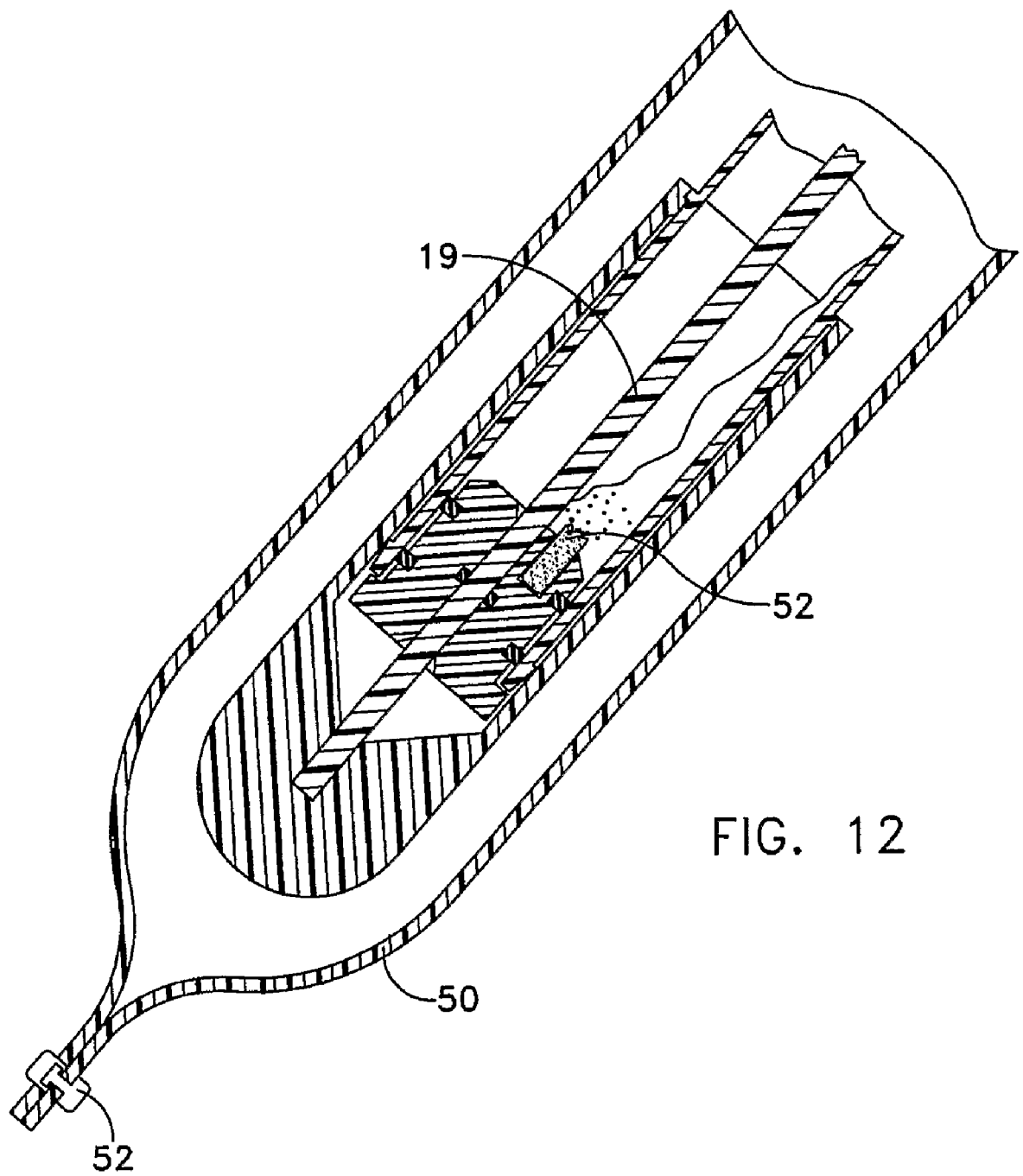
FIG. 12 is a cross-sectional view of the swab cover shown in the use position and oriented so that material from the test vial can flow back to contact the disinfectant that is shown attached at the bottom of the plug.

FIG. 12 shows the test unit cover in position to allow material from the test vial to contact the disinfectant tablet 52.

Figure 13:
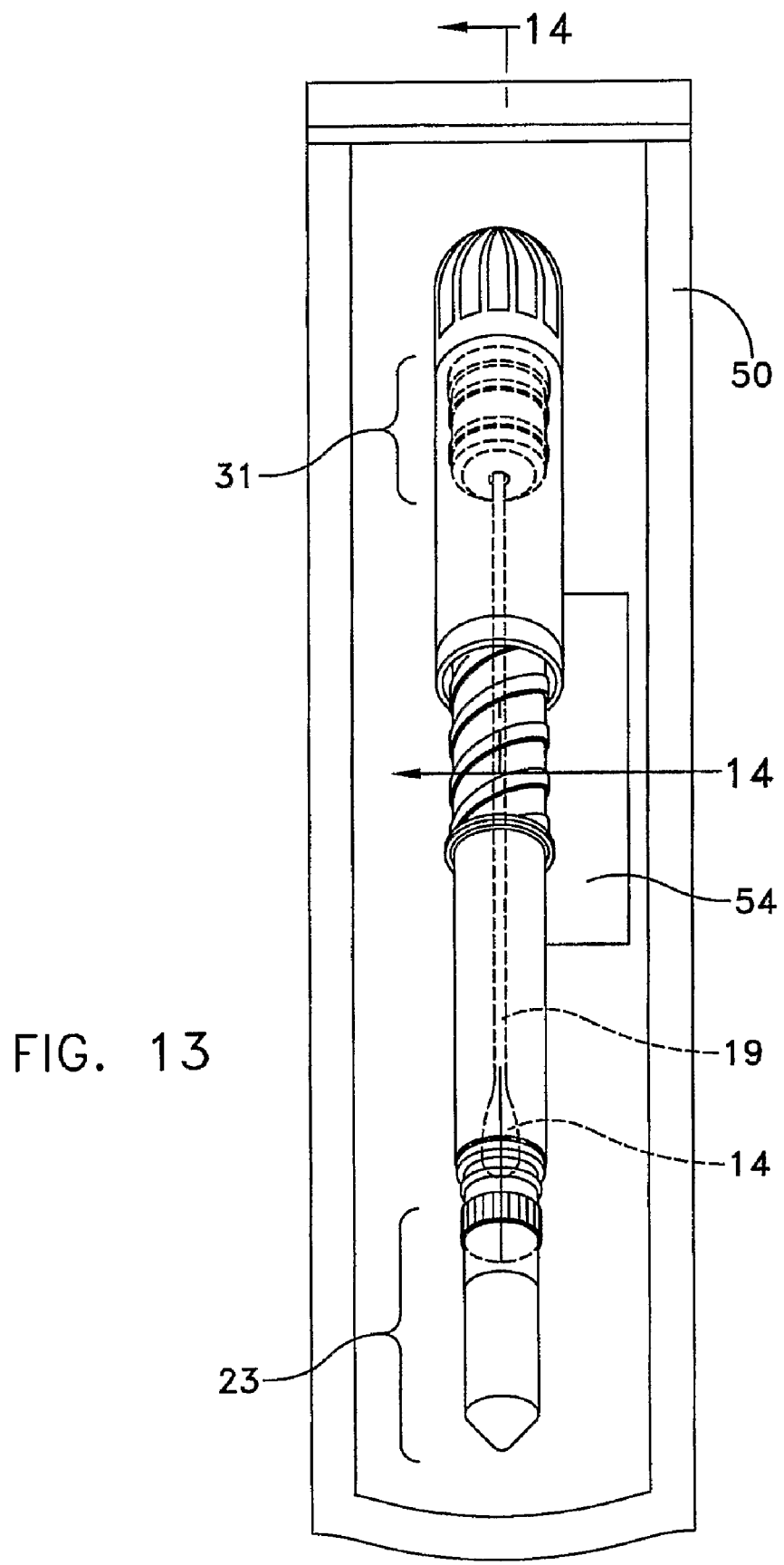
FIG. 13 is a perspective partial elevation of the test unit in the pre-use position within the containment bag that also includes a disinfectant pouch.

FIG. 13 shows the test unit within a sealed containment bag with a disinfectant pouch 54 that contains the disinfectant that can be released to contact reagents and sample released from the test vial after testing.

Figure 14:
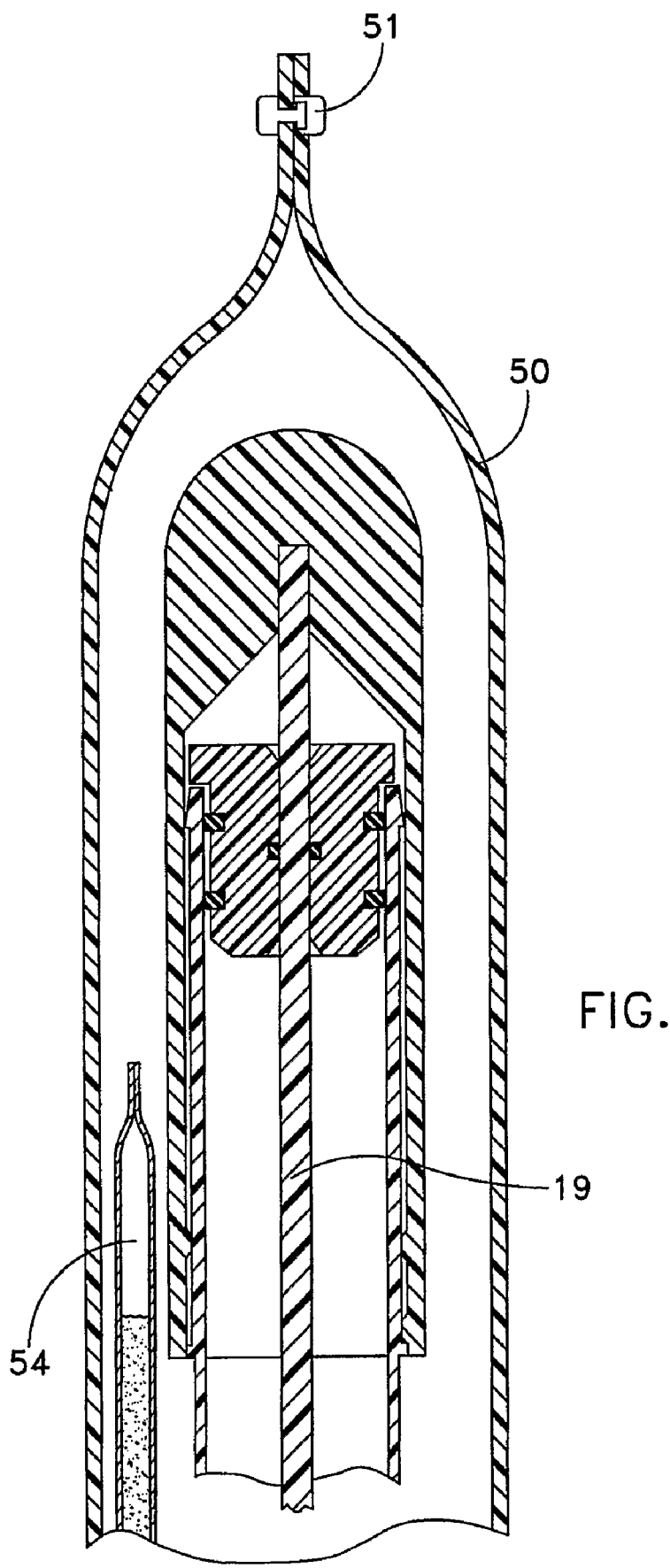
FIG. 14 is a cross-sectional view of the swab cap and a disinfectant pouch within a containment bag.

FIG. 14 shows the cross-section of FIG. 13 including disinfectant pouch.

Figure 15:
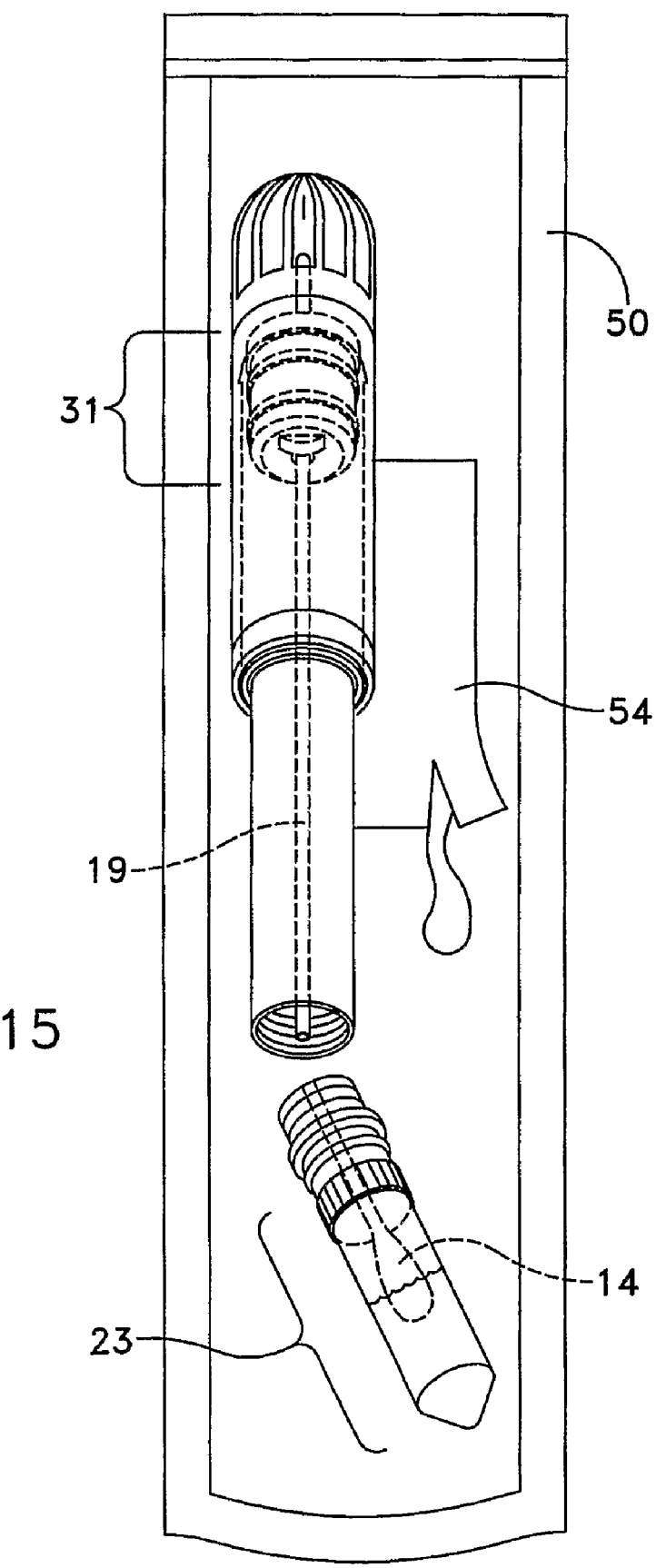
FIG. 15 is a perspective and partial elevation view of the test unit with the test vial removed from the body of the test unit to allow the test material to contact the disinfectant released from the disinfectant pouch.

FIG. 15 shows the post-testing disengagement of the test vial from the test unit body to allow material from the test vial to contact disinfectant released from the disinfectant bag. Although probe head 14 is shown separate from probe shaft 19, such scenario is not required.

Figure 16:
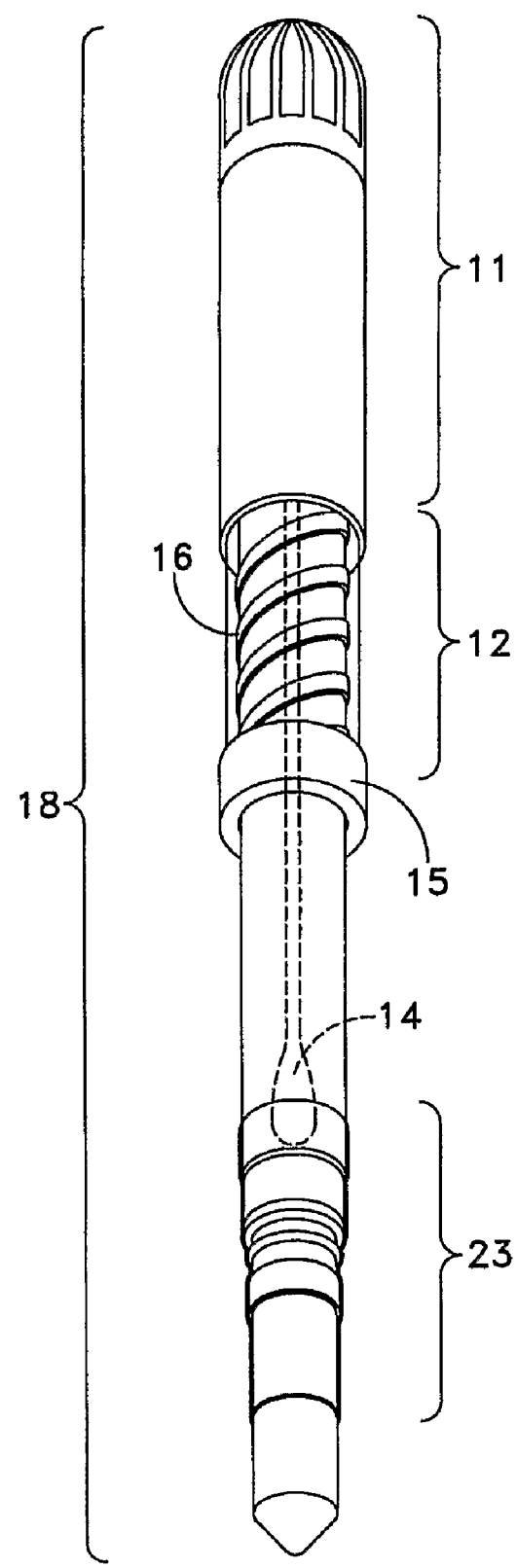
FIG. 16 is a perspective view including a partial elevation view of a test unit with a probe in the pre-use position within the test unit and including a removable sleeve and o-ring holder.

FIG. 16 shows an embodiment with the probe 14 in the pre-use position within the test unit 18. The probe 14 is attached to the cover 11 which, in the pre-use position is above threads 16. A removable sleeve 12 covering the threads 16 prevents the cover 11, with threads therein, from prematurely engaging the threads 16 on the test unit body and prematurely moving into the use position. The removable sleeve 12 is shown resting in an o-ring holder 15 that is in a press-fit arrangement on the test unit 18. A test vial 23 is secured to the bottom of the unit 18.

Figure 17:
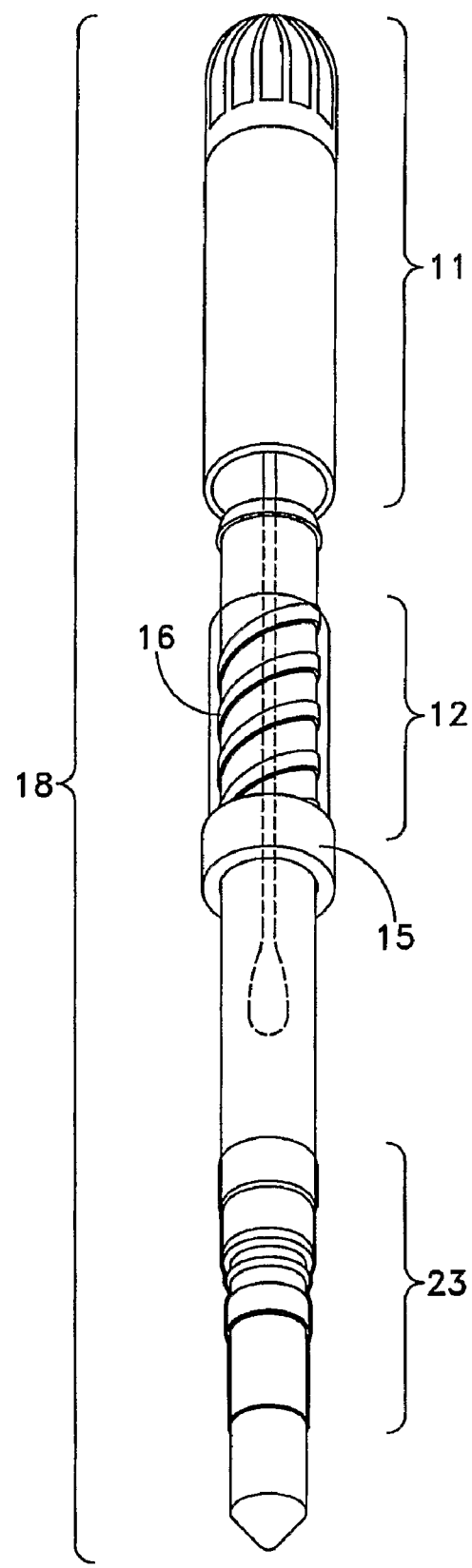
FIG. 17 is a partially exploded perspective view of a test unit with cover partially disengaged from the test unit body.

FIG. 17 shows a partially exploded perspective view of the unit 18 of FIG. 16 with cover 11 disengaged from the test unit body and away from the removable sleeve 12 so that the sleeve can be removed prior to engaging the threads 16.

Figure 18:
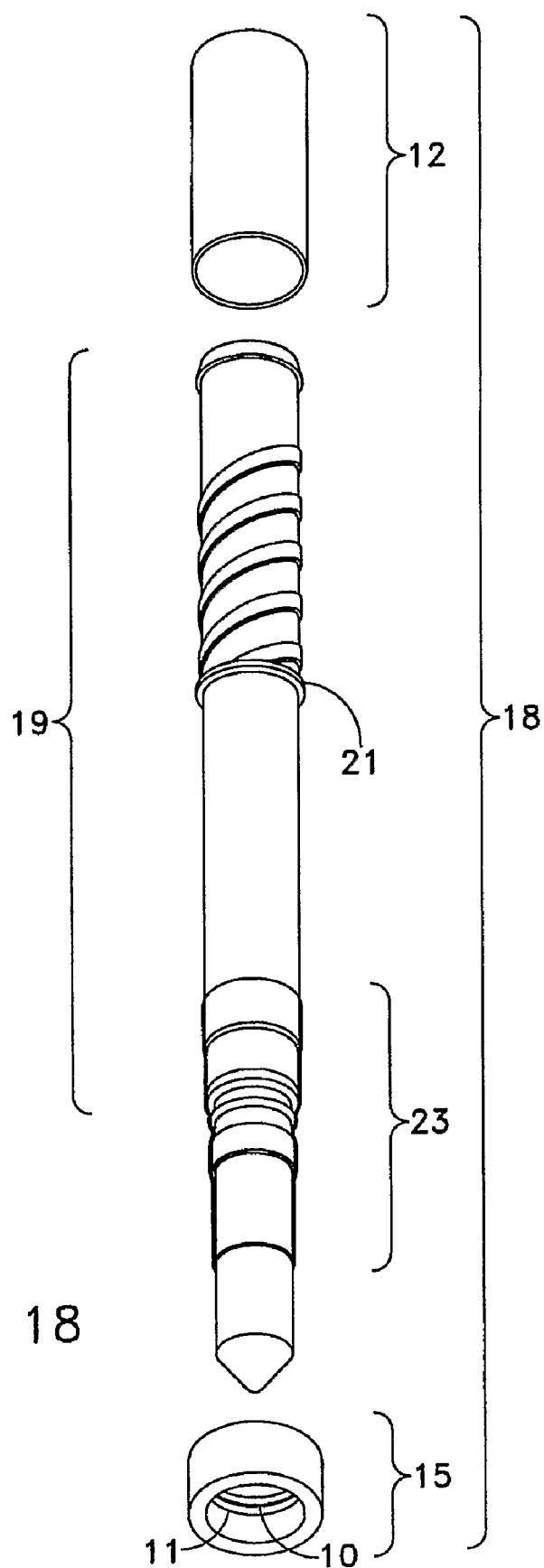
FIG. 18 is a partially exploded perspective view of a test unit showing the test unit body without the cover and showing the removable sleeve and o-ring holder.

FIG. 18 is a partially exploded perspective view of the unit 18 of FIG. 16 showing the test unit body 19 without the cover and the removable sleeve 12 and o-ring holder 15 separated from the test unit. The o-ring holder 15 includes an o-ring 10 for engaging the cover and a shoulder/ridge 11 to enable the o-ring holder 5 to be press-fit against the shoulder/ridge 12.

FIG. 19 is an enlarged partial cross-sectional view of the unit of FIG. 16 in the pre-use position showing an o-ring 20 within an o-ring holder 15 around the test unit. Also shown is the o-ring holder 15 press-fit over the test unit with a shoulder/ridge 21 within the o-ring holder 15 press-fit against the shoulder/ridge on the test unit. The removable sleeve 12 is also shown within the o-ring holder 15.

FIG. 20 is an enlarged partial cross-sectional view of the cover 11 with removable sleeve 12 preventing engagement of the cover 11.

FIG. 21 is an enlarged partial cross-sectional view showing the o-ring 20, o-ring holder 15 and shoulder/ridge 21 to allow the o-ring holder 15 to be press-fit onto the unit. The removable sleeve 12 is also shown within the o-ring holder 15.

Figure 22:
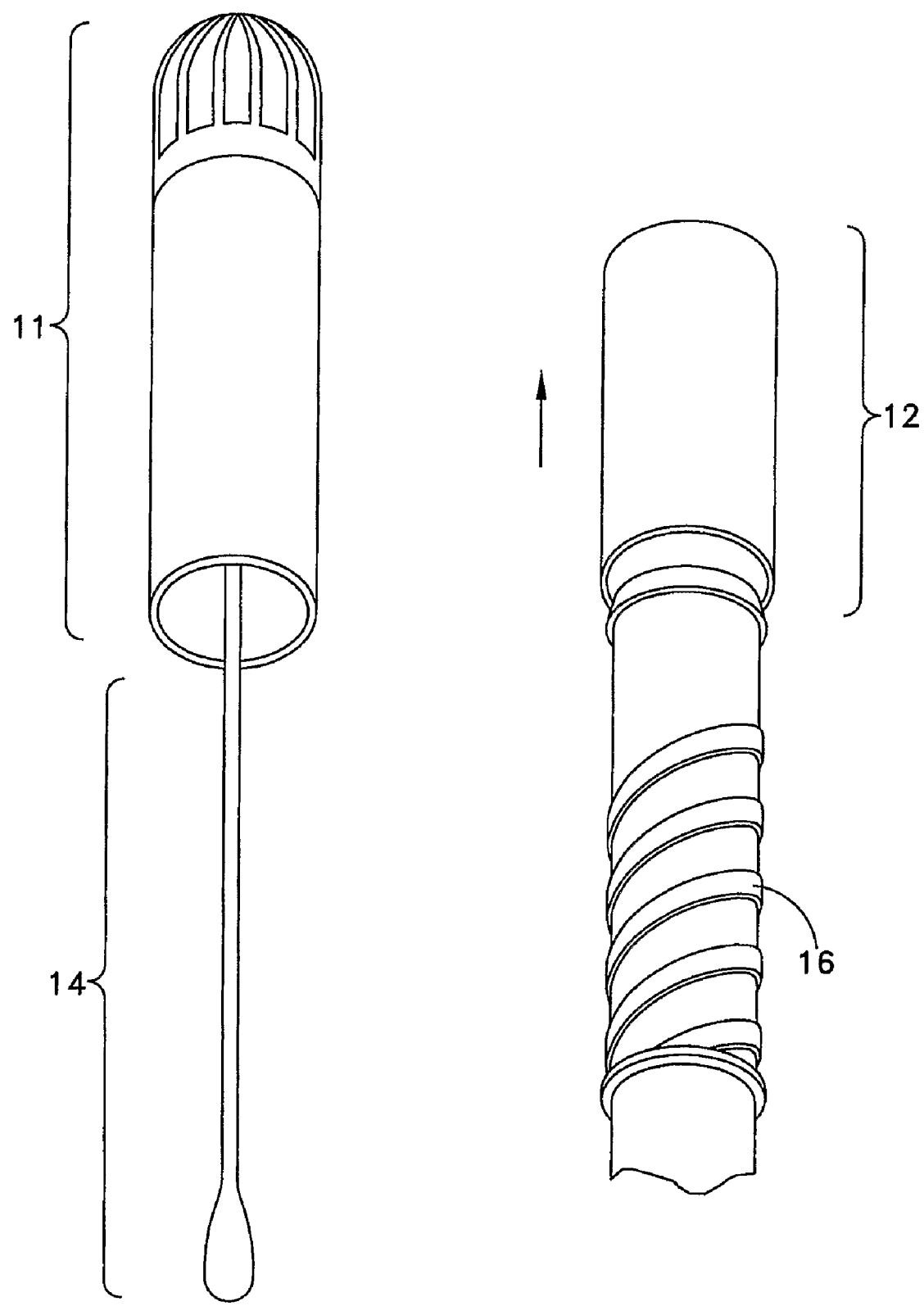
FIG. 22 is an exploded perspective view of a swab cover with probe and hollow body section of a test unit with probe removed from the body.

FIG. 22 is a perspective view of the unit of FIG. 16 showing the cover 11 with probe 14 removed from the body and removable sleeve 12 being removed from the test unit body to allow threadable engagement.

Figure 23:
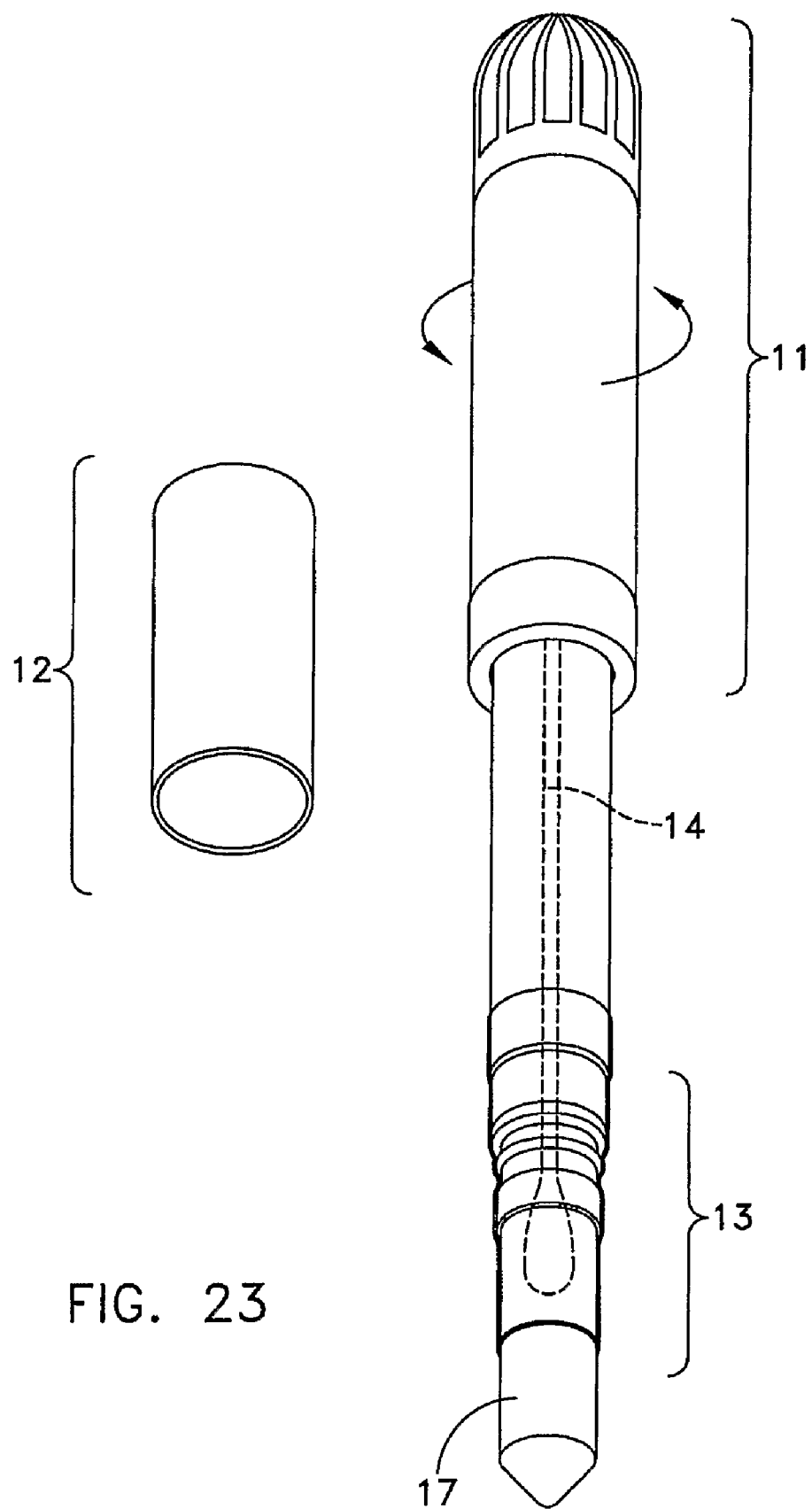
FIG. 23 is a perspective view including partial elevation view of a test unit with removable sleeve removed and probe engaged into a test vial.

FIG. 23 is a perspective view and partial elevation view of the unit of FIG. 16 with removable sleeve 12 removed and probe 14 engaged into the test vial 23. The probe 14 punctures the one or more frangible seals of the test vial 23 to contact the reagents 17 within the test vial 23.

Figures 24, 25:
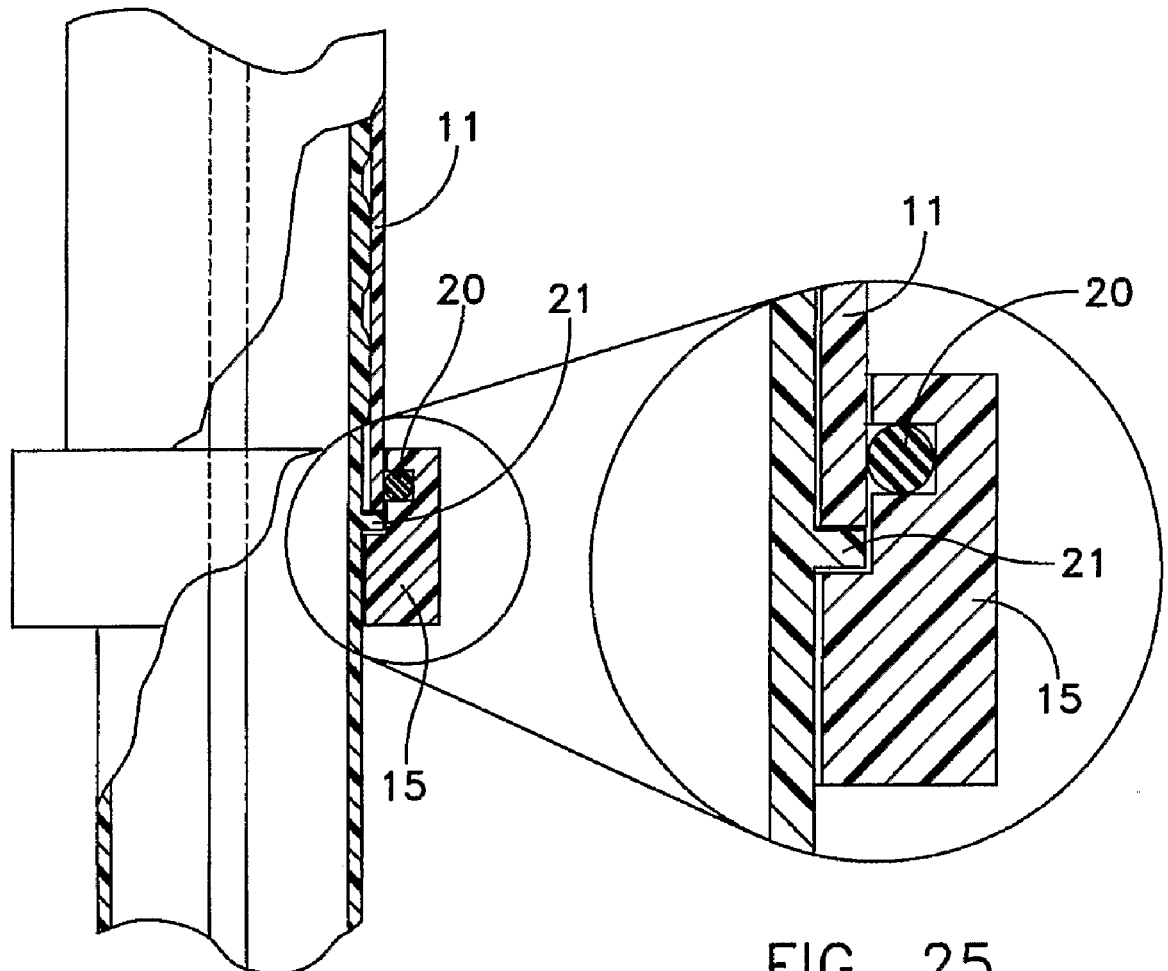
FIG. 24 is an enlarged partial cross-sectional view of a test unit in the post-use, engaged/closure position.
FIG. 25 is an enlarged partial cross-sectional view of a section of FIG. 24.

FIG. 24 is an enlarged partial cross-sectional view of the unit shown in FIG. 16 with the o-ring holder 15 and o-ring 20 with cover 11 engaged into the o-ring 20, in the post-use position. The removable sleeve 12 has been removed.

FIG. 25 is an enlarged partial cross-sectional view of a section of FIG. 24 showing the o-ring 20 within o-ring holder 15 and cover 11.

Figure 26:
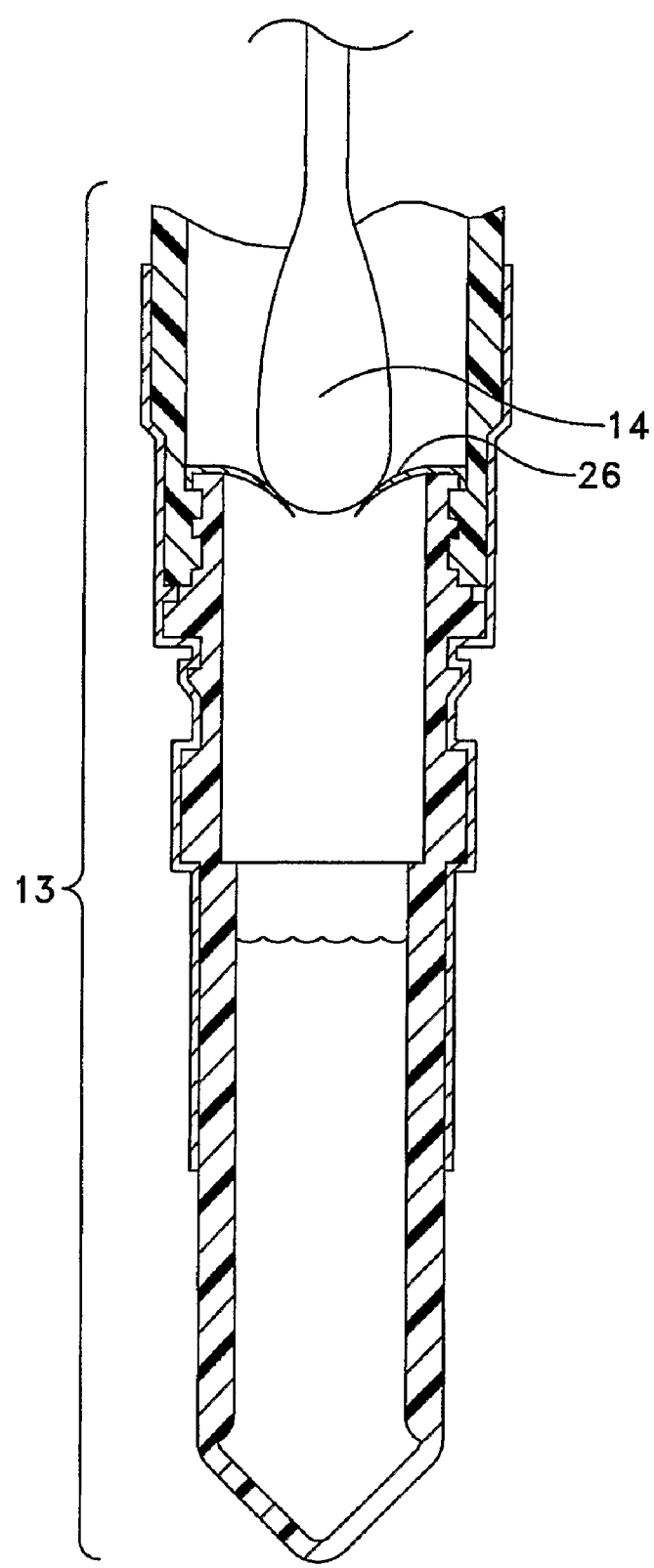
FIG. 26 is cross-sectional view of the bottom portion of a test unit with probe puncturing the frangible seal on a test vial.

FIG. 26 is a partial cross-sectional view of the bottom portion of the unit shown in FIG. 16 with probe 14 puncturing the frangible seal 26 on the test vial 23.

Figure 27:
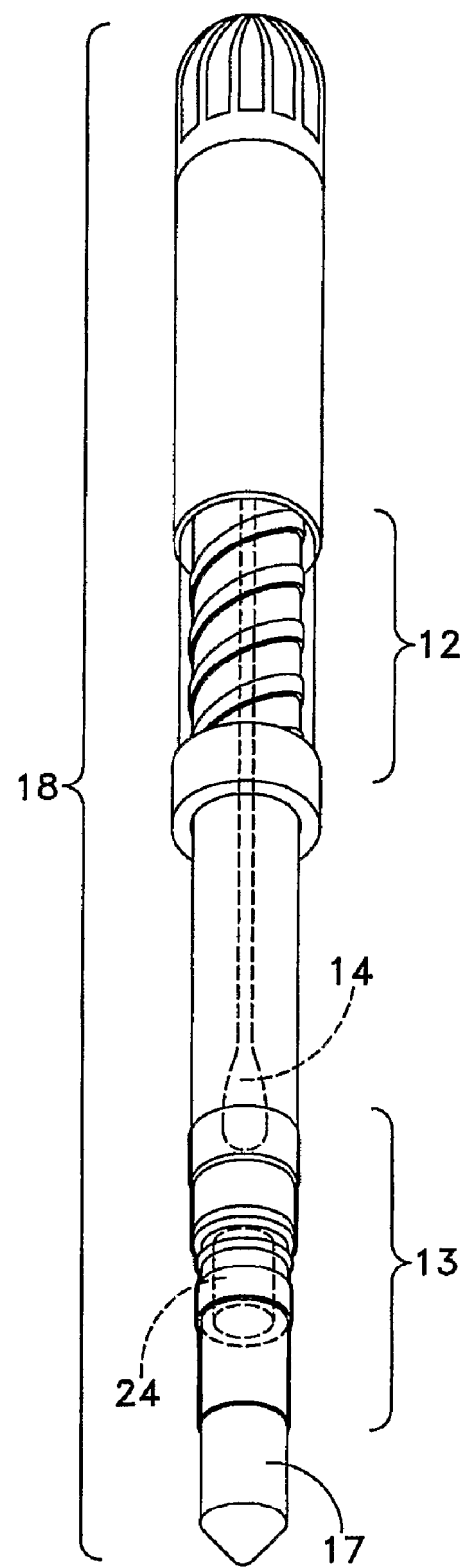
FIG. 27 is a perspective view including a partial elevation view of a test unit with a probe in the pre-use position within a test unit and with optional niblet within the test vial.

FIG. 27 is a perspective view including a partial elevation view of a test unit 18 with a probe 14 in the pre-use position within the test unit 18. Also shown is an optional niblet 24 containing additional reagents separated from the reagents 17 at the bottom of the test vial 23.

Figure 28:
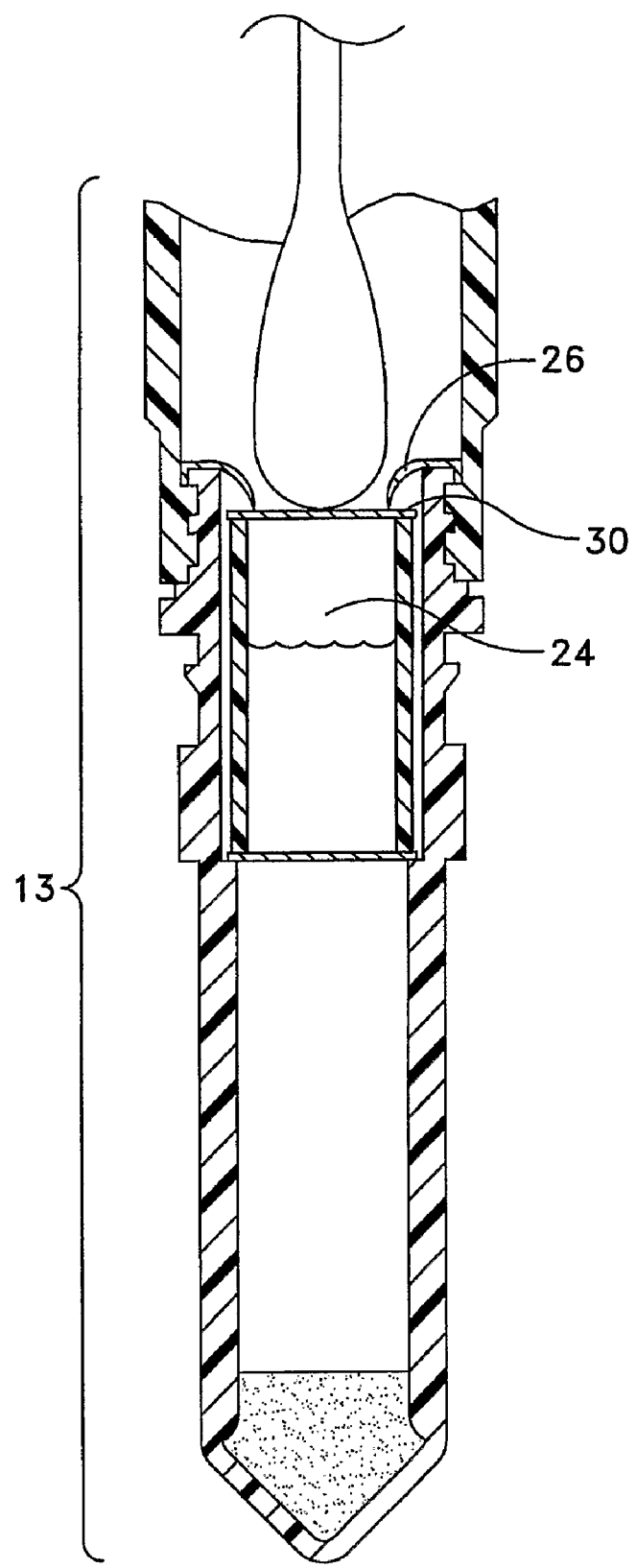
FIG. 28 is cross-sectional view of the bottom portion of a test unit with probe puncturing the frangible seal on the test vial and in position to puncture the first frangible seal of an optional niblet.

FIG. 28 is cross-sectional view of the bottom portion of the unit shown in FIG. 27 with probe puncturing the frangible seal 26 on the test vial 23 and in position to puncture the first frangible seal 30 of the optional niblet 24.

Figure 29:
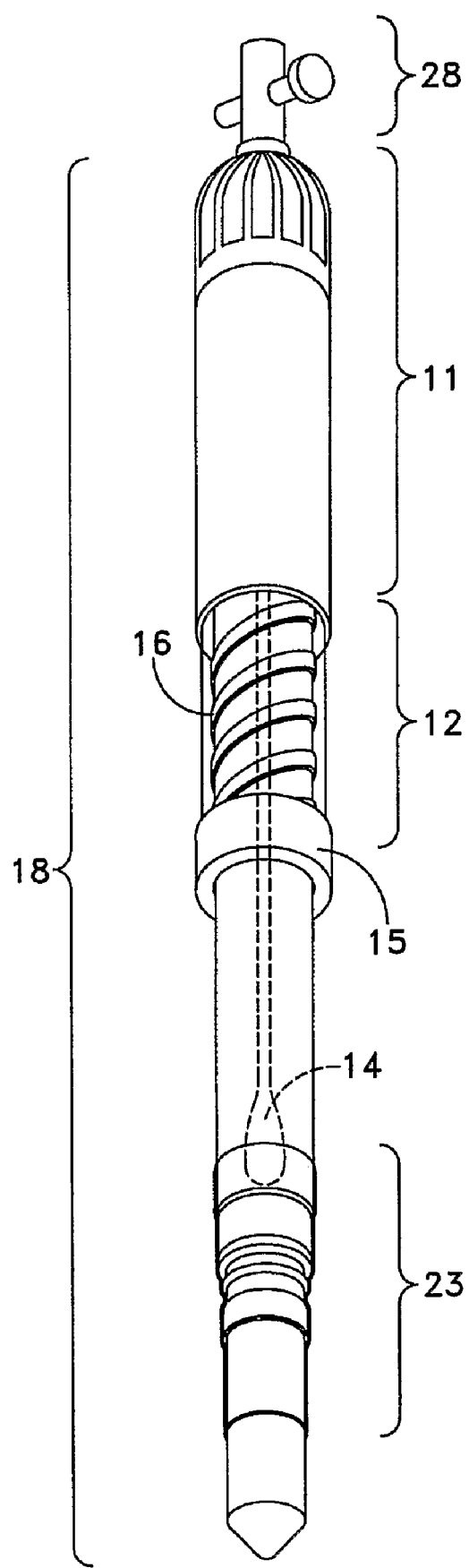
FIG. 29 is a perspective view including a partial elevation view of a test unit with a probe in the pre-use position within the test unit and an outlet/inlet valve through which the environment within the test unit can be adjusted and maintained.

FIG. 29 is a perspective view including a partial elevation view of a test unit 18 with a probe 14 in the pre-use position within the test unit 18. Also shown is an outlet/inlet valve 28 through which the environment within the test unit can be adjusted and maintained, for example through the removal of oxygen or the addition of nitrogen. The optional one or more niblets 24 can also be included with additional reagents.

The invention claimed is:

1. A method for detecting an analyte in a sample, the method comprising:
  a) providing an elongated test unit, the test unit comprising:
    (i) a hollow section having a first open end and second open end; (ii) a probe within the hollow section, the probe comprising a first probe end and a second probe end; (iii) a test unit cover, the cover adapted to enclose said first open end of the hollow section and positioned relative to the probe so that the longitudinal movement of the cover causes the longitudinal movement of the probe; (iv) a test vial extending from the second open end of the hollow section, and containing a reagent sealed therein by a frangible seal; (v) an o-ring surrounding the test unit and within an o-ring holder, the o-ring and o-ring holder configured so that the longitudinal movement of the cover secures the cover into the o-ring holder and in position so that the cover abuts the o-ring, said abutting of the o-ring by the cover forming a liquid barrier which barrier prevent liquid from leaking out of the test unit,
    the test unit constructed and arranged to obtain a test sample on or within the second probe end and to provide admixture of the sample with the reagent within the test vial;
  b) removing the probe from the test unit;
  c) collecting a sample onto the probe to provide a sample-probe;
  d) inserting the sample-probe into the test unit;
  e) moving the sample-probe longitudinally through the frangible test vial seal to contact the reagent,
    wherein moving the sample-probe longitudinally both ruptures a frangible seal and secures the cover within the o-ring holder wherein the cover abuts the o-ring.

2. The method of claim 1 wherein the test unit further comprises a plug, the plug attached to said sample-probe and configured so that the longitudinal movement of the sample-probe positions the plug so that the plug form a liquid seal between the peripheral wall of the plug and the inner diameter wall of the hollow section of the test unit, wherein said liquid seal prevents a liquid within the test unit from leaking out of the test unit.

3. The method of claim 2 further comprising providing a disinfectant tablet attached to the plug and positioned to be contacted by the reagent and the sample after testing.

4. The method of claim 1 wherein the probe comprises a shaft with a swab at the second probe end.

5. The method of claim 1 wherein the reagent comprises media for growth of a microorganism.

6. The method of claim 5 wherein said microorganism comprises a pathogen.

7. The method of claim 5 wherein said microorganism comprises *Listeria monocytogenes*.

8. The method of claim 5 wherein said microorganism comprises a phage.

9. The method of claim 1 wherein the reagent comprises media for growth of a microorganism and further comprise a colorimetric indicator of the presence or absence of said microorganism.

10. The method of claim 1 further comprising providing a removable sleeve, the sleeve surrounding the test unit and adapted to prevent the premature longitudinal movement of the probe.

11. The method of claim 1 further comprising providing a niblet within the test vial, the niblet containing a reagent to be combined with the reagent within the test vial.

12. The method of claim 1 wherein the first probe end is attached to the test unit cover.

13. An elongate test unit for detecting an analyte in a sample comprising:
  a) a hollow section, the hollow section comprising a first open end and a second open end;

b) a probe within the hollow section, the probe comprising a first probe end and a second probe end the second probe end adapted for obtaining a test sample;

c) a test vial extending from the second open end of the hollow section, the test vial adapted to store a reagent and sealed by a frangible seal, wherein when the probe is moved longitudinally the second probe end ruptures the frangible seal;

d) a test unit cover, the cover adapted to enclose said first open end of the hollow section and positioned relative to the first probe end so that the longitudinal movement of the cover causes the longitudinal movement of the probe, the longitudinal movement resulting in both the rupture of the frangible seal and the abutting of the cover with an o-ring within an o-ring holder, the o-ring holder and o-ring positioned on the outside wall of the test unit body, the test unit constructed and arranged to obtain a test sample on the probe and to provide admixture of the sample on the probe with the reagent within the test vial and wherein the abutting of the cover with the o-ring prevents liquid from leaking out from the test unit.

14. The test unit of claim 13 further comprising a plug, the plug attached to said sample-probe and configured so that the longitudinal movement of the sample-probe positions the plug so that the plug forms a liquid seal between a peripheral wall of the plug and a inner diameter wall of the hollow section of the test unit, and further comprising a bore extending therethrough, the plug bore having an entrance end and an exit end, the plug bore being shaped to receive the probe and configured to form a liquid seal between the peripheral wall of the probe and the internal wall of the plug, wherein when the probe is moved longitudinally the second probe end ruptures the frangible seal and the plug forms the liquid seal between the peripheral wall of the plug and the inner diameter wall of the hollow section of the test unit.

15. The test unit of claim 14 wherein the liquid seal between the peripheral wall of the probe and the internal wall of the plug comprise an o-ring.

16. The test unit of claim 14 wherein the liquid seal between the peripheral wall of the plug and the internal wall of the hollow section of the test unit comprises an o-ring.

17. The test unit of claim 13 wherein the reagents comprise media for growth of a microorganism.

18. The test unit of claim 17 wherein said microorganism comprises a pathogen.

19. The test unit of claim 17 wherein said microorganisms comprises *Listeria monocytogenes*.

20. The test unit of claim 13 wherein said reagents comprise media for growth of a microorganism and further comprise a colorimetric indicator of the presence or absence of said microorganism.

21. The test unit of claim 13 further comprising providing a removable sleeve, the sleeve adapted to prevent the premature longitudinal movement of the probe.

22. The test unit of claim 13 wherein the second probe end comprises an absorbent tip configured to absorb a sample from a surface.

* * * * *